(12) United States Patent
Scaccabarozzi et al.

(10) Patent No.: US 10,571,432 B2
(45) Date of Patent: Feb. 25, 2020

(54) METHODS, SYSTEMS, AND DEVICES FOR SOLID AXLE TESTING

(71) Applicant: General Electric Company, Schenectady, NY (US)

(72) Inventors: Luca Scaccabarozzi, Hurth (DE); Tobias Bruch, Hurth (DE)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 15/690,621

(22) Filed: Aug. 30, 2017

(65) Prior Publication Data

US 2018/0059061 A1 Mar. 1, 2018

Related U.S. Application Data

(60) Provisional application No. 62/381,712, filed on Aug. 31, 2016.

(51) Int. Cl.
*G01N 29/04* (2006.01)
*G01N 29/22* (2006.01)
*G01N 29/26* (2006.01)
*G01N 29/28* (2006.01)

(52) U.S. Cl.
CPC ......... *G01N 29/043* (2013.01); *G01N 29/223* (2013.01); *G01N 29/262* (2013.01); *G01N 29/28* (2013.01); *G01N 2291/0234* (2013.01); *G01N 2291/0289* (2013.01); *G01N 2291/0421* (2013.01); *G01N 2291/0422* (2013.01); *G01N 2291/262* (2013.01); *G01N 2291/2698* (2013.01)

(58) Field of Classification Search
CPC ...... G01N 29/04; G01N 29/043; G01N 29/24; G01N 29/221; G01N 29/223; G01N 29/225; G01N 29/2487; G01N 29/26; G01N 29/262; G01N 29/265; G01N 29/28; G01N 2291/044; G01N 2291/2693; G01N 2291/2696; G01N 2291/105; B60B 2900/541; B60B 35/12; B60B 2900/3316; B60Y 2200/30; B61F 99/00; B61F 15/02; B61F 15/00
USPC .......... 73/627, 620, 622, 623, 625, 641, 644
See application file for complete search history.

(56) References Cited

U.S. PATENT DOCUMENTS

| | | | |
|---|---|---|---|
| 3,685,350 A * | 8/1972 | Pettinato | G01N 29/24 310/336 |
| 4,899,590 A | 2/1990 | Light et al. | |
| 5,131,276 A | 7/1992 | Kibblewhite | |
| 5,708,208 A | 1/1998 | Bonitz | |
| 7,735,370 B2 | 6/2010 | Burat et al. | |

(Continued)

FOREIGN PATENT DOCUMENTS

| | | |
|---|---|---|
| EP | 2 546 642 A2 | 1/2013 |
| WO | WO-2015145303 A2 | 10/2015 |

OTHER PUBLICATIONS

Liaptsis, Dimos. "Development of a Phased Array Inspection System for the Testing of Railway Solid Axles from the End Face." Infrastructures de transport, Mar. 21, 2014.

(Continued)

*Primary Examiner* — Suman K Nath
(74) *Attorney, Agent, or Firm* — Mintz Levin Cohn Ferris Glovsky and Popeo, P.C.

(57) ABSTRACT

Methods, systems, and devices for solid axle testing are provided.

21 Claims, 23 Drawing Sheets

(56) References Cited

U.S. PATENT DOCUMENTS

| | | | |
|---|---|---|---|
| 8,336,383 B2 | 12/2012 | Lesage et al. | |
| 9,027,405 B2 | 5/2015 | Desai et al. | |
| 2004/0207394 A1* | 10/2004 | Harthorn | G01B 17/02 324/216 |
| 2011/0296923 A1* | 12/2011 | Cataldo | G01N 29/043 73/632 |
| 2013/0068026 A1* | 3/2013 | Kitazawa | G01N 29/043 73/602 |
| 2013/0220018 A1* | 8/2013 | Kollgaard | G01N 29/04 73/618 |
| 2017/0106881 A1* | 4/2017 | Cantini | B60B 17/00 |

OTHER PUBLICATIONS

Liaptsis, Dimosthenis et al. "The application of phased array ultrasonic techniques for inspection of railway axles from their end face." NDT 2010 Conference, 2010.

TWI Ltd. AxleInspect—"Development of novel inspection technique for train axles." 2014.

TWI Ltd. "Development of phased array ultrasonic testing inspection system for testing solid railway axles." TWI, Dated no later than Aug. 1, 2016, www.twi-global.com/news-events/case-studies/development-of-phased-array-ultrasonic-testing-inspection-system-for-testing-solid-railway-axles-570/.

GE. "Solid Axle Inspection with Phases array Ultrasonic Cone Probe." Dated no later than Aug. 1, 2016.

Peng, C. et al. "High-Power Locomotive Solid Axle Defect on-Line Detection Technique." 18th WCNDT, Durban, Apr. 16, 2012.

Sicard, R. et al. "Phased Array Scanner Head for train Axle Inspection." 18th WCNDT, Durban, Apr. 16, 2012.

International Invitation to Pay Additional Fees issued in connection with corresponding PCT Application No. PCT/US17/49597 dated Nov. 13, 2017.

International Search Report and Written Opinion issued in connection with corresponding PCT Application No. PCT/US17/49597 dated Jan. 11, 2018.

\* cited by examiner

METHODS, SYSTEMS, AND DEVICES FOR SOLID AXLE TESTING

CROSS REFERENCE

The present application claims priority to U.S. Provisional Patent Application No. 62/381,712 entitled "Methods, Systems, And Devices For Solid Axle Testing" filed Aug. 31, 2016, which is hereby incorporated by reference in its entirety.

FIELD

The present disclosure relates generally to methods, systems, and devices for solid axle testing.

BACKGROUND

Currently, solid axles for trains are inspected from their front faces using single-element ultrasonic (UT) probes with different angles or phased array (PA) UT probes with an electronic steering capability. During the inspection the axles are typically already mounted on the trains and equipped with relevant components, for example, wheelsets, brake disks, transmission disks, etc.

Inspection of the axles requires that as much volume as possible of the axle is inspected. However, in most cases, the axle's skin surface is protected with a thick paint that makes a proper UT coupling impossible. The only free access point for inspection is thus the axle's front face. However, as shown in FIG. 1, threaded holes 10 formed in an axle's front face for fixing a cap to the axle prevent certain areas or angular sectors 12 from being inspected. PA probes currently exist which can be inserted in a cone-shaped stud hole 14 formed in a front of face of an axle, as illustrated in FIG. 2, but these probes can only be used for testing the front journal or the wheel set area of the axle, and it is not possible to cover the body of the axle (e.g., the central part of the axle's shaft).

During inspection with single-element UT probes, A-Scan data is conventionally used in testing, which limits the comprehensive documentation of the testing results. Additionally, due to the limited amount of inspection angles used, and thus limited testing coverage, indications may be missed or wrongly estimated. Since the inspection with single-element UT probes requires a repetition of the axle for each probe, the testing with the probes is typically time consuming.

Also, a challenge in the inspection of solid axles from the front joint either by PA or single-element UT probe are geometrical reflections from the axle itself which may mimic or hide reflection signals from relevant indications and the multiple reflections plus mode conversions which may cause false indications.

Accordingly, there remains a need for improved methods, systems, and devices for solid axle testing.

BRIEF DESCRIPTION

Methods, systems, and devices for solid axle testing are provided.

In one embodiment, an inspection system is provided that includes a probe configured to be inserted into a blind hole formed in a solid axle. The probe includes an ultrasonic transducer at an end face thereof that is configured to generate ultrasonic waves in the solid axle covering substantially an entire portion of the solid axle to be inspected when the probe is within the blind hole.

The inspection system can have any number of variations. As an example, the ultrasonic transducer can include an angle beam ultrasonic transducer configured to propagate a shear wave and a longitudinal beam ultrasonic transducer configured to propagate a compression wave, and the ultrasonic waves can include the shear wave propagated by the angle beam ultrasonic transducer and the compression wave propagated by the longitudinal beam ultrasonic transducer. As another example, the ultrasonic transducer can include a plurality of phased array transducers configured to operate with different wave modes and configured to provide a zone-discrimination employed an actuation and evaluation unit during position encoded recording of a B-Scan of the axle's skin surface. As yet another example, the ultrasonic transducer can include a single ultrasonic transducer. As another example, the probe can be configured to be inserted into the blind hole until the end face of the probe abuts a bottom surface of the blind hole. As still another example, the probe can include a controller configured to analyze the echo to determine whether a flaw is present in the solid axle. The flaw can include at least one of a crack, a notch, an inclusion, a void, and a fracture. As yet another example, the substantially entire portion of the solid axle to be inspected can be at least one of substantially an entire skin surface of the solid axle and substantially an entire volume of the solid axle. As another example, the probe can be configured to be inserted into the blind hole at any rotational orientation relative to the solid axle. As still another example, the probe can be configured to be automatically centered within the blind hole when inserted therein. As yet another example, the solid axle can be mounted on a train.

As yet another example, the probe can include a securing element configured to secure the probe within the blind hole. The securing element can include at least one magnet configured to magnetically engage the solid axle to effect the securing, and/or the probe can include a movable handle configured to be moved to selectively cause the securing element to secure the probe within the blind hole. The movable handle can be configured to cause the securing element to selectively move the securing element toward the solid axle and away from the solid axle.

As yet another example, the inspection system can include a liquid couplant on the end face of the probe. The liquid couplant can include one of water, grease, oil, and a gel.

As another example, the blind hole can be in a front face of the solid axle. The front face can have a plurality of threaded holes formed therein, and the probe can be configured to be inserted into the blind hole beyond a depth of each of the plurality of threaded holes. The probe can be configured to be inserted into the blind hole to abut an end surface of the blind hole.

In another embodiment, an inspection method is provided that includes inserting a probe into a blind hole formed in a solid axle, and activating an ultrasonic transducer of the probe to cause ultrasonic waves to propagate within the solid axle covering at least one of substantially an entire skin surface of the solid axle and substantially an entire volume of the solid axle.

The inspection method can have any number of variations. As an example, the ultrasonic transducer can include an angle beam ultrasonic transducer and a longitudinal beam transducer, and the ultrasonic waves can include a shear wave propagated by the angle beam ultrasonic transducer and a compression wave propagated by the longitudinal beam ultrasonic transducer. As another example, the ultrasonic transducer can include a plurality of phased array transducers configured to operate with different wave modes and configured to provide a zone-discrimination employed in the phase array ultrasonic electronics during position encoded recording of a B-scan of the axle's skin surface. As yet another example, the ultrasonic transducer can include a single ultrasonic transducer. As still another example, the probe can be inserted into the blind hole until an end face of the probe abuts a bottom surface of the blind hole. As yet another example, the probe can be configured to be inserted into the blind hole at any rotational orientation relative to the solid axle. As still another example, the probe can be automatically centered within the blind hole when inserted therein. As another example, the solid axle can be mounted on a train.

As another example, the inspection method can include detecting an echo of the ultrasonic waves, and analyzing the echo to determine whether a flaw is present in the solid axle. The flaw can include at least one of a crack, a notch, an inclusion, a void, and a fracture.

As yet another example, the probe can include a securing element that automatically secures the probe within the blind hole. The securing element can include at least one magnet configured to magnetically engage the solid axle to effect the automatic securing, and/or the inspection method can include manually moving a handle of the probe with the movement of the handle automatically causing the securing element to secure the probe within the blind hole. The movement of the handle can cause the securing element to move toward the solid axle. The inspection method can also include manually moving the handle again to move the securing element away from the solid axle and thereby release the securing.

As still another example, a liquid couplant can be provided on an end face of the probe. The liquid couplant can include one of water, grease, oil, and a gel.

As another example, the blind hole can be in a front face of the solid axle. The front face can have a plurality of threaded holes formed therein and the probe can be inserted into the blind hole beyond a depth of each of the plurality of threaded holes, and/or the probe can be inserted into the blind hole to abut an end surface of the blind hole.

As yet another example, the inspection method can include removing the probe from the blind hole, inserting the probe into a second blind hole formed in a second solid axle, and activating the ultrasonic transducer of the probe to cause ultrasonic waves to propagate within the second solid axle covering at least one of substantially an entire skin surface of the solid axle and substantially an entire volume of the solid axle. The solid axle and the second solid axle can be mounted on a wheel of a train.

BRIEF DESCRIPTION OF THE DRAWING

This disclosure will be more fully understood from the following detailed description taken in conjunction with the accompanying drawings, in which.

Figure 1:
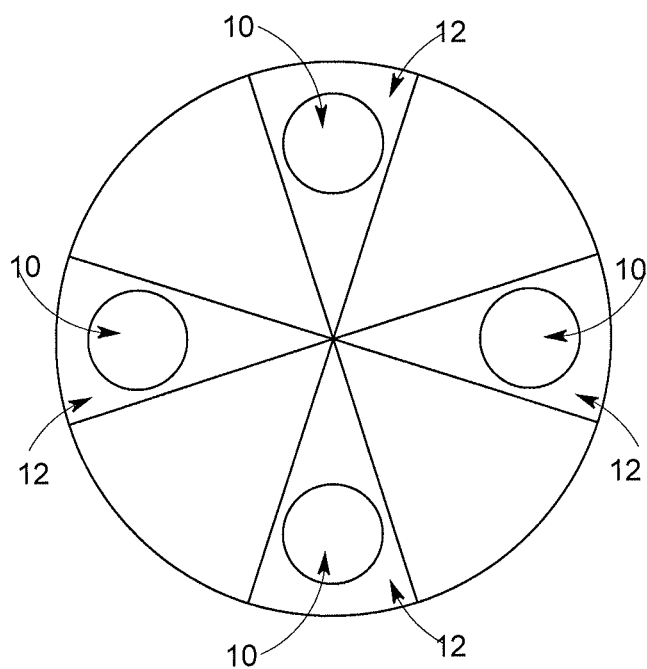
FIG. 1 (Prior Art) is a schematic front view of an embodiment of a front face of a solid axle.
Figure 2:
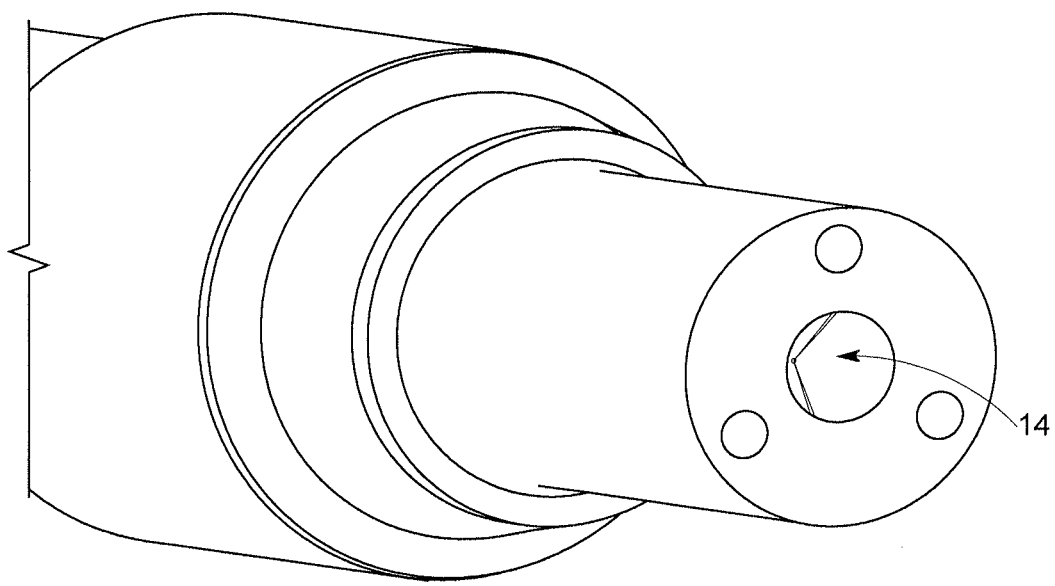
FIG. 2 (Prior Art) is a perspective view of a front portion of an embodiment of a solid axle.

It is noted that the drawings are not necessarily to scale. The drawings are intended to depict only typical aspects of the subject matter disclosed herein, and therefore should not be considered as limiting the scope of the disclosure. In the drawings, like numbering represents like elements between the drawings.

DETAILED DESCRIPTION

Certain exemplary embodiments will now be described to provide an overall understanding of the principles of the structure, function, manufacture, and use of the systems, devices, and methods disclosed herein. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape.

Methods, systems, and devices for solid axle testing are provided. In general, a probe can be configured to operatively engage a solid axle to inspect the solid axle, such as by being inserted into a hole formed in a front face of the solid axle. The probe can be configured to operatively engage the solid axle when the solid axle is already mounted in position for use, such as by being mounted on a train and equipped with relevant components, such as wheel-sets, brake disks, or transmission disks. The probe can include at least one ultrasonic transducer configured to generate ultrasonic waves in the solid axle, when the probe is operatively coupled to the axle's front face. The at least one ultrasonic transducer can include a phased array (PA) ultrasonic transducer, and the ultrasonic waves can be configured to propagate at different steering angles in the axle substantially covering an entire portion of the solid axle, e.g., substantially 100% of the solid axle's skin surface and/or substantially 100% of the solid axle's volume. A person skilled in the art will appreciate that the ultrasonic waves may not cover precisely 100% of the skin surface or 100% of the volume but nevertheless be considered to cover substantially the entire skin surface or the entire volume due to acceptable tolerance for beam spread or geometrically shadowed areas.

According to the type of flaw to be detected, the inspection can be performed to detect targets on the solid axle's skin surface or/and within the volume of the solid axle. Flaws such as fatigue cracks which typically propagate from the axle's external surface, e.g., skin surface, are exemplary targets for the inspection. This technology is not limited to fatigue crack inspection as the technology described may be applied to inspection of a variety of targets including, as non-limiting examples, other types of cracks, notches, inclusions, voids, and fractures. Any descriptions below in which one kind of inspection is discussed should not be interpreted as a limiting example/application.

Figure 3:
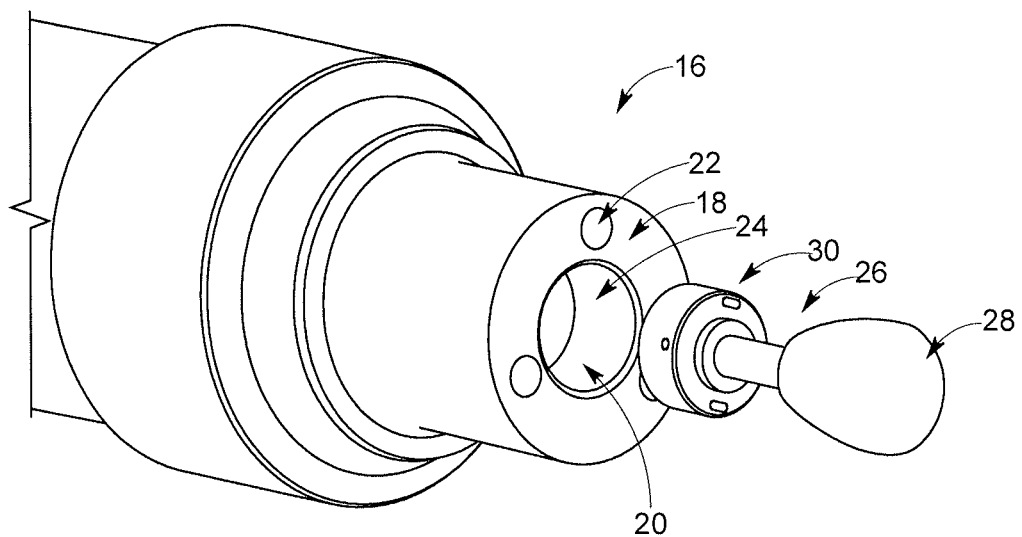
FIG. 3 is a perspective view of an embodiment of a probe and a front portion of another embodiment of a solid axle.
Figure 4:
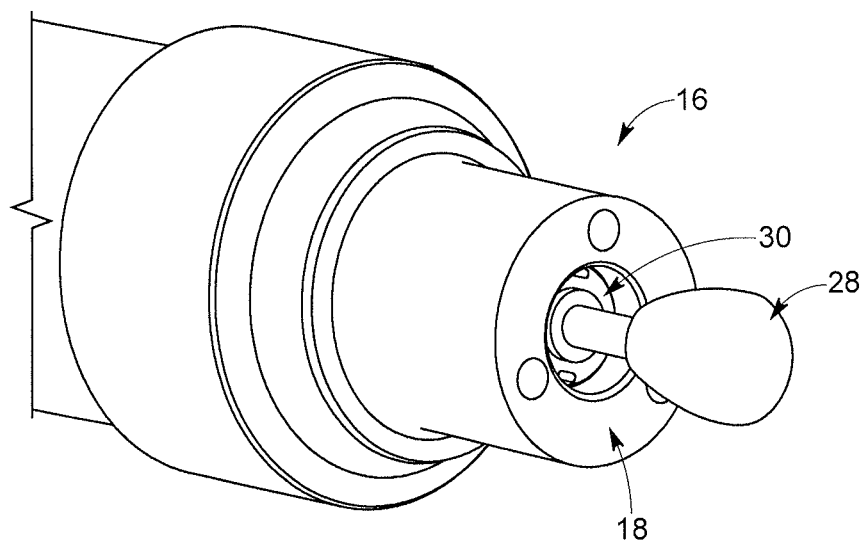
FIG. 4 is a perspective view of the probe of FIG. 3 operatively coupled to the solid axle.

The methods, systems, and devices provided herein can be used with a variety of solid axles. The solid axles can be solid axles for railway trains or for other industrial objects that include solid axles, such as subway trains, aircraft, construction vehicles, and the like. FIGS. 3 and 4 illustrate one embodiment of a solid axle 16 with which the methods, systems, and devices provided herein can be used. The solid axle 16 has a front face 18 with a central stud hole 20 formed therein and a plurality of threaded holes 22 formed therein. The solid axle 16 has three threaded holes 22 but can include another number of threaded holes. The stud hole 20 is a blind hole and has a cylindrical shape that defines a substantially flat end face 24 of the stud hole 20. A person skilled in the art will appreciate that the end face 24 may not be precisely flat but nevertheless be considered to be substantially flat due to any of a variety of factors, such as manufacturing tolerances and sensitivity of measurement equipment. The end face 24 of the stud hole 20 being flat may facilitate operative engagement with a substantially flat end face of a probe inserted into the stud hole.

The probes described herein can have a variety of configurations. FIGS. 3 and 4 illustrate one embodiment of a probe 26 configured to facilitate inspection of a solid axle. The probe 26 is illustrated in FIGS. 3 and 4 with the solid axle 16 but can be similarly used with other embodiments of solid axles. The probe 26 has a handle 28 at a proximal end thereof that is configured to be held by hand to facilitate manual manipulation of the probe 26. The handle 28 has a bulb shape to facilitate gripping thereof, but the handle 28 can have other shapes.

Figure 5:
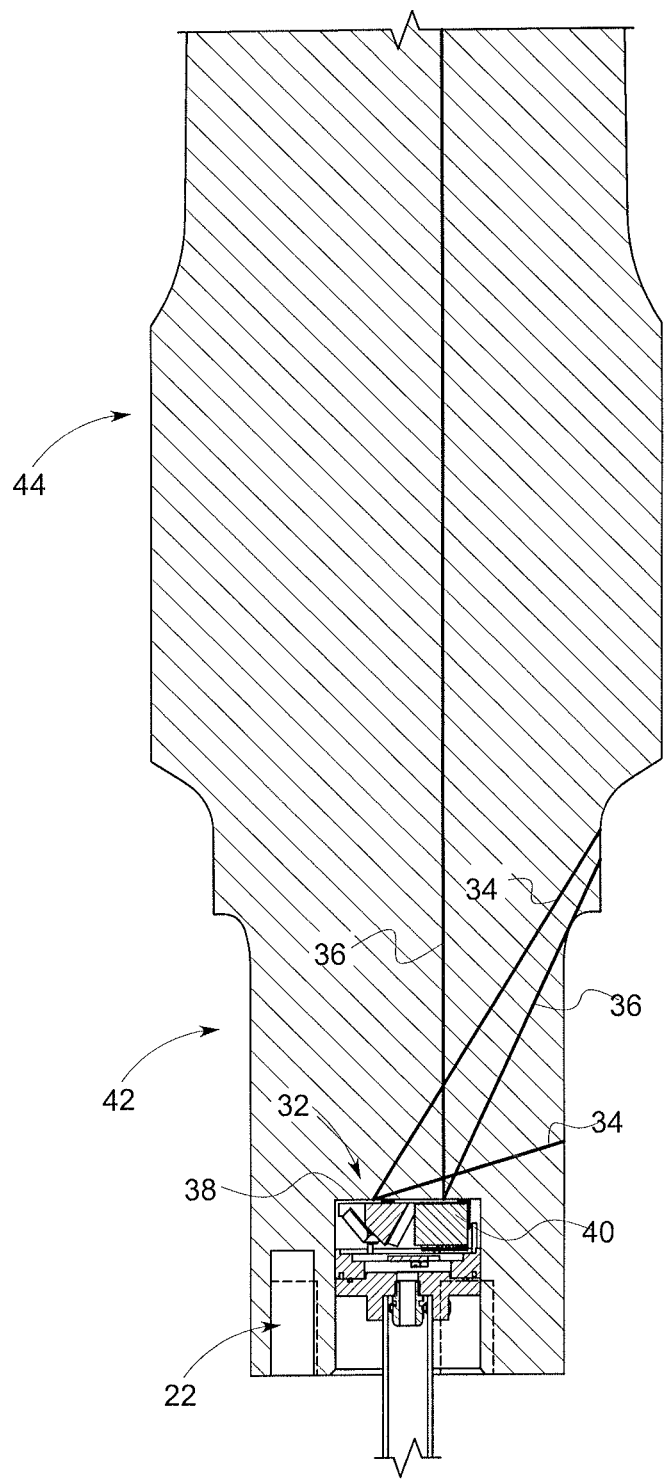
FIG. 5 is a side cross-sectional view of the probe and solid axle of FIG. 4.

The probe 26 also has an inspection portion 30 at a distal end thereof. The inspection portion 30 is configured to be inserted into a stud hole of a solid axle, as shown in FIG. 4 in which the inspection portion 30 of the probe 26 is disposed within the stud hole 20. An end face 32 (FIG. 5) of the probe 26 is configured to abut the end face 24 of the stud hole 20, as shown in FIGS. 4 and 5 in which the end faces 24, 32 contact one another such that surfaces of the probe 26 and the axle 16 are in contact with one another. Because the stud hole 20 has a depth greater than a depth of each of the threaded holes 22, as shown in FIG. 5, the end face 32 of the probe 26 is located within the axle 16 a distance beyond an end of the threaded holes 22 when the end faces 24, 32 abut one another. The threaded holes 22 may therefore not interfere with an ultrasonic wave 34, 36 propagated by one or more ultrasonic transducers 38, 40 at the end face 32 of the probe 26 in the inspection portion 30.

The one or more ultrasonic transducers 38, 40 can have a variety of configurations. In an exemplary embodiment, the one or more ultrasonic transducers 38, 40 are each an ultrasonic (UT) PA transducer. In this illustrated embodiment, one of the ultrasonic transducers 38 is an angle beam UT PA transducer configured to generate and detect shear waves 34 at different steering angles, and another one of the ultrasonic transducers 40 is a longitudinal beam UT PA transducer configured to generate and detect compression waves 36 at different steering angles. The ultrasonic waves generated by the one or more ultrasonic transducers 38, 40 thus includes the shear waves 34 and the compression waves 36. The combination of the ultrasonic waves 34, 36 allows the probe to generate ultrasonic waves at different steering angles which cover substantially an entire skin surface of the axle 16, as shown in FIG. 5, thereby allowing inspection of substantially the entire skin surface. In other words, substantially an entire circumference of the axle 16 may be inspected along a longitudinal length of the axle 16.

Figure 6:
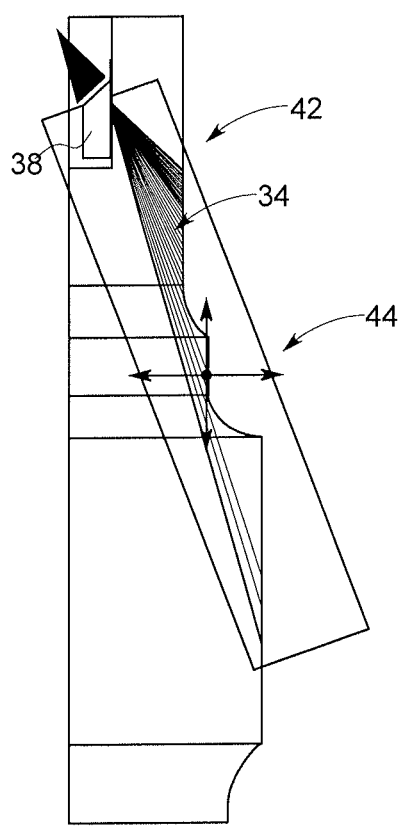
FIG. 6 is a schematic cross-sectional view of ultrasonic waves propagating at different steering angles in a front portion of the solid axle of FIG. 3.
Figure 7:
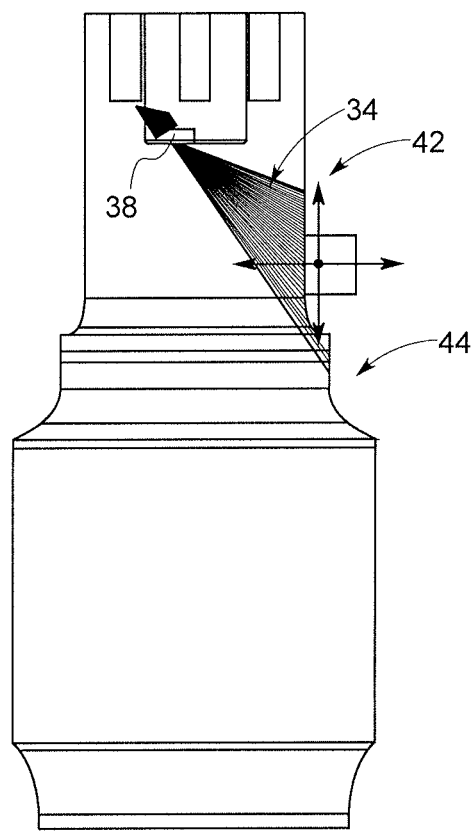
FIG. 7 is a schematic cross-sectional view of ultrasonic waves propagating at different steering angles from a different emission point in a front portion of the solid axle of FIG. 3.
Figure 8:
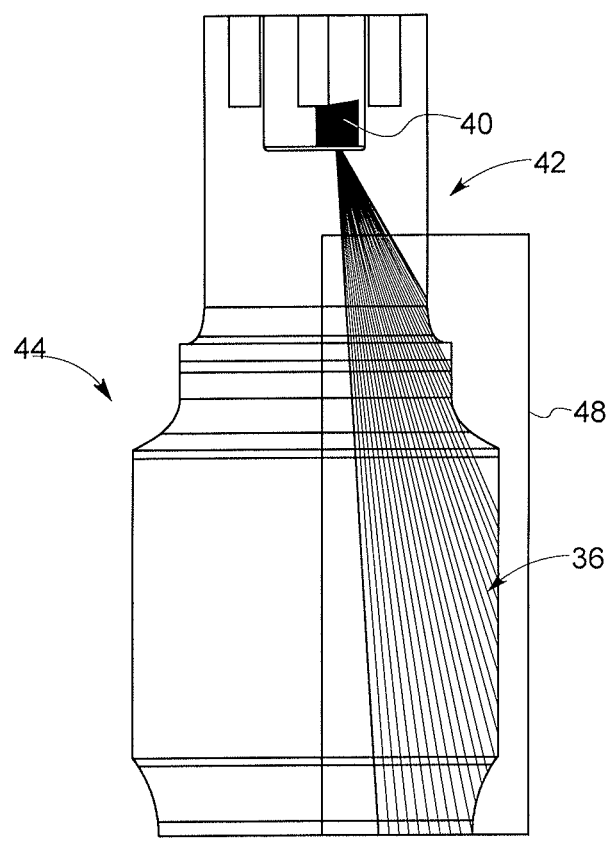
FIG. 8 is a schematic cross-sectional view of ultrasonic waves propagating at different steering angles in a front portion of the solid axle of FIG. 3.
Figure 9:
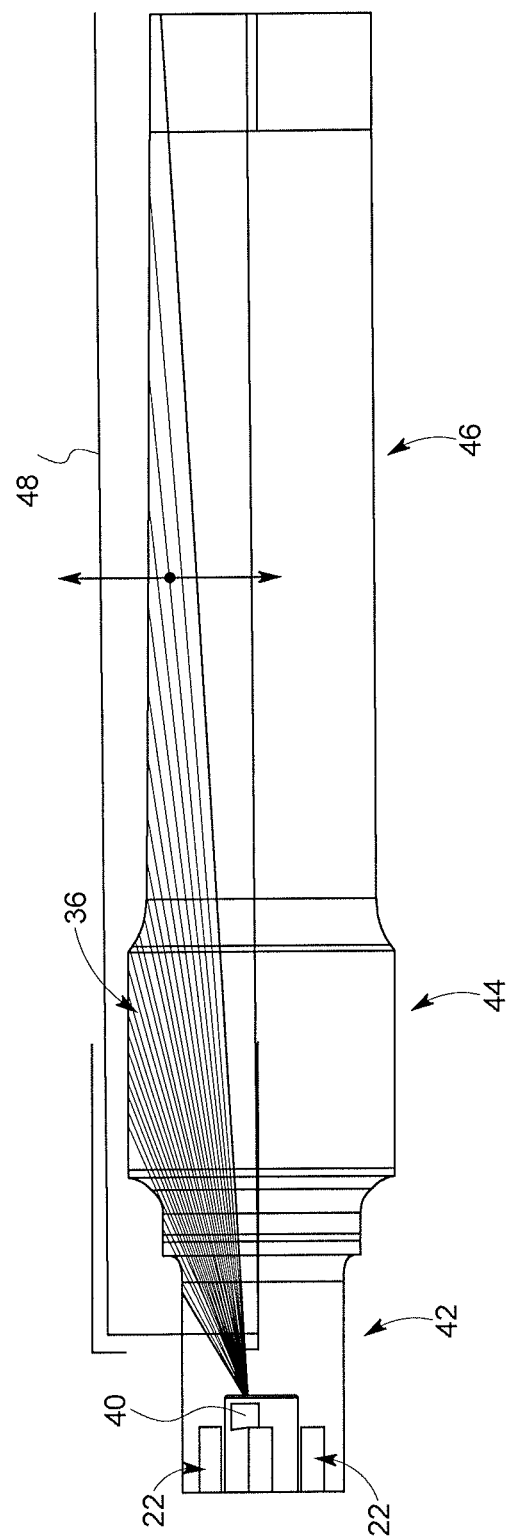
FIG. 9 is a schematic cross-sectional view of the ultrasonic waves of FIG. 8 propagating in the solid axle.

FIG. 6 illustrates one embodiment of the angle beam UT PA transducer 38 generating the shear waves 34 in one approach for inspection of a journal portion 42 of the axle 16 and a wheel seat portion 44 of the axle 16. FIG. 7 illustrates another embodiment of the angle beam UT PA transducer 38 propagating the shear waves 34 in another approach for inspection of the journal portion 42. FIGS. 8 and 9 illustrate one embodiment of the longitudinal beam UT PA transducer 40 generating the compression waves 36 in one approach for inspection of the journal portion 42, a wheel seat portion 44, and a body portion 46 of the axle 16.

Figure 10:
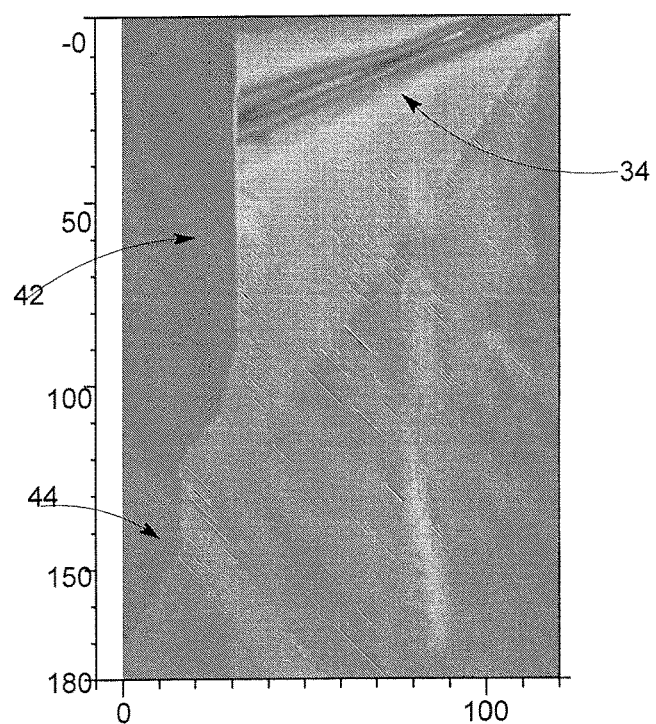
FIG. 10 is an image of sound pressure distribution of an ultrasonic wave propagating at a specific steering angle in a front portion of the solid axle of FIG. 3.
Figure 11:
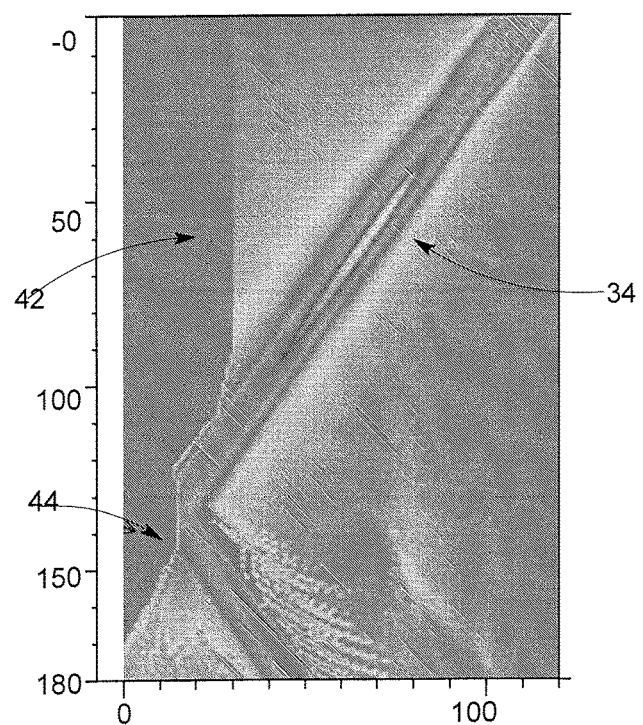
FIG. 11 is another image of sound pressure distribution of an ultrasonic wave propagating at a specific steering angle in a front portion of the solid axle of FIG. 3.

The angle of the shear wave 34 generated by the angle beam UT PA transducer 38 can vary and can be controlled electronically by an actuation and evaluation unit. In an exemplary embodiment, the angle of the shear wave 34 is in a range of about 33° to 70°, e.g., about 35°, about 65°, about 70°, in a range of about 35° to 70°, etc. A person skilled in the art will appreciate that an angle may not have a precise degree value but nevertheless be considered to be at about that degree value due to any of a variety of factors, such as manufacturing tolerances of the ultrasonic transducer and knowledge of the sound velocities. An entirety of the solid axle's skin surface circumference can be scanned by rotating the probe 26 360° within the solid axle's stud hole, such as by manually rotating the probe 26 by hand. FIG. 10 illustrates one embodiment of an angle of the shear wave 34, with the angle being about 70°, with the shear wave 34 engaging the axle's journal portion 42 to facilitate inspection thereof. FIG. 11 illustrates another embodiment of an angle of the shear wave 34, with the angle being about 35°, with the shear wave 34 engaging the axle's wheel seat portion 44 to facilitate inspection thereof.

Figure 12:
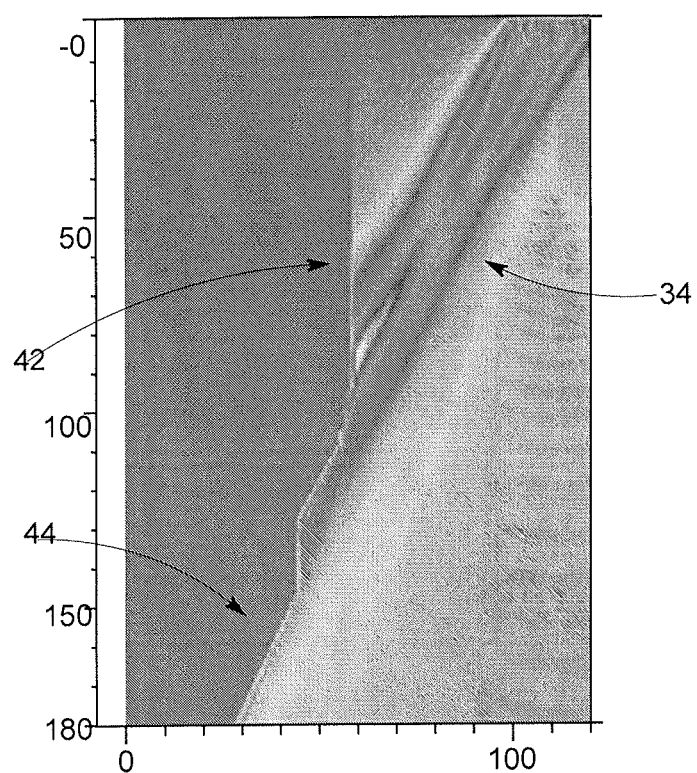
FIG. 12 is yet another image of sound pressure distribution of ab ultrasonic wave propagating at a specific steering angle in a front portion of the solid axle of FIG. 3.
Figure 13:
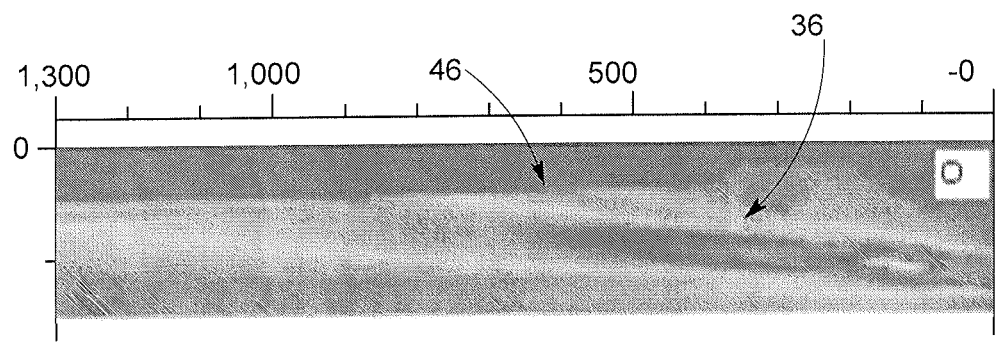
FIG. 13 is still another image of sound pressure distribution of an ultrasonic wave propagating at a specific steering angle in a front portion of the solid axle of FIG. 3.

The angle of the compression wave 36 generated by the longitudinal beam UT PA transducer 40 can vary and can be controlled electronically by an actuation and evaluation unit. In an exemplary embodiment, the angle of the compression wave 36 is in a range of about 0° to 30°, e.g., in a range of about 2° to 25°, in a range of about 2° to 30°, etc. FIG. 12 illustrates one embodiment of an angle of the compression wave 36, with the angle being about 30°, with the compression wave 36 engaging the axle's journal portion 42 and wheel seat portion 44 to facilitate inspection thereof. FIG. 13 illustrates another embodiment of an angle of the compression wave 36, with the angle being about 3°, with the compression wave 36 engaging the axle's body portion 46 to facilitate inspection thereof.

As shown in FIGS. 11 and 12, the angle of the shear wave 34 and compression wave 36 can be configured such that they probe the same area of the solid axle 16. Thus, by employing the angle beam UT PA transducer 38 and the longitudinal UT PA transducer 40 the complete skin surface of the axle 16 can be inspected, as illustrated in FIGS. 10-13.

Figure 14:
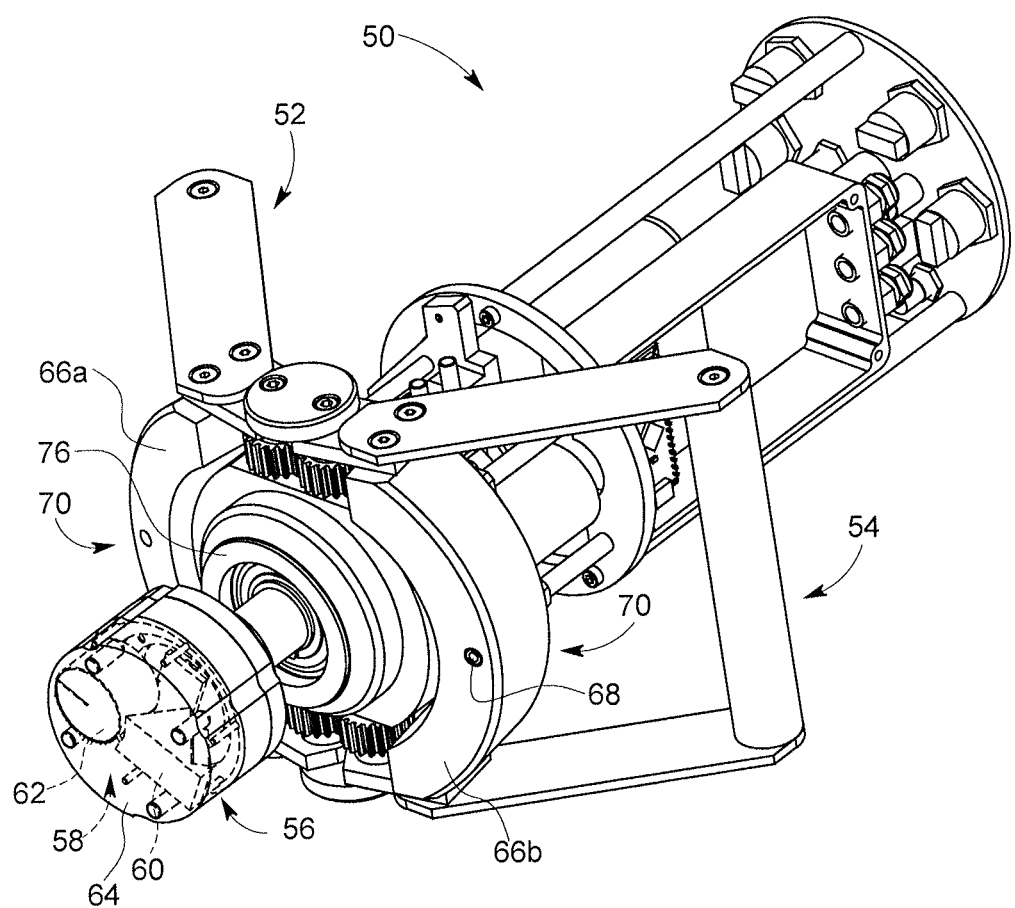
FIG. 14 is a perspective view of another embodiment of a probe.
Figure 15:
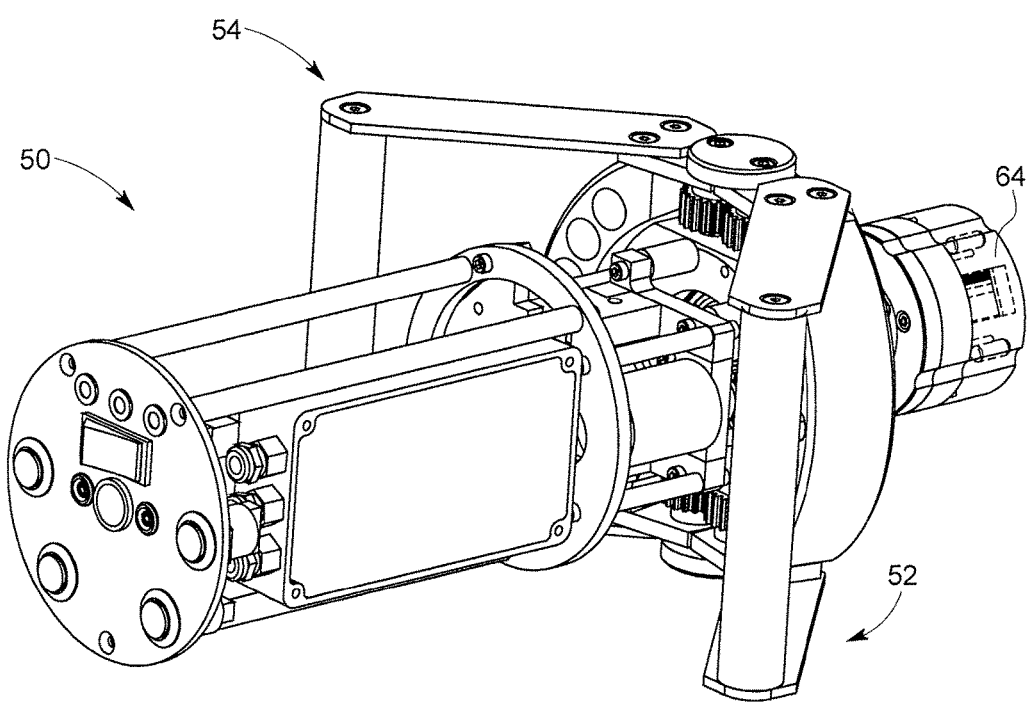
FIG. 15 is another perspective view of the probe of FIG. 14.
Figure 16:
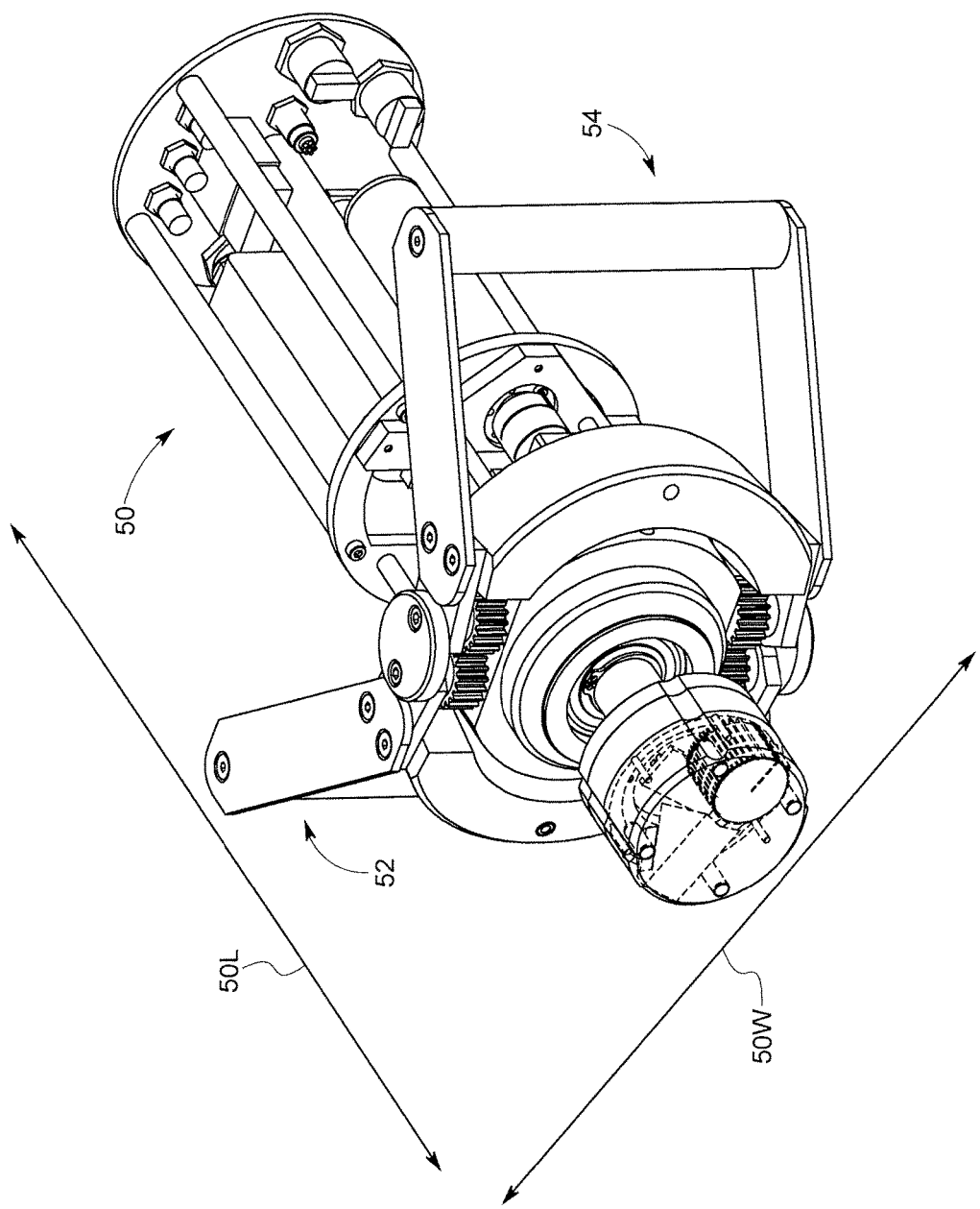
FIG. 16 is yet another perspective view of the probe of FIG. 14.

FIGS. 14-16 illustrate another embodiment of a probe 50 configured to facilitate inspection of a solid axle. The probe 50 can generally be configured and used similar to the probe 26 of FIGS. 3 and 4. The probe 50 can have a variety of sizes. As shown in FIG. 16, the probe 50 has a length SOL and a width 50W. In one embodiment, the length SOL is about 350 mm and the width 50W is about 250 mm.

The probe 50 is configured to be portable such that a user may transport the probe 50 between inspection sites. A weight of the probe 50 may facilitate the portability, such as the probe 50 being relatively lightweight, e.g., in a range of about 4 to 5 kg.

The probe 50 has a handle that includes first and second movable handles 52, 54 each configured to held by one hand of a user to facilitate manual manipulation of the probe 50. The handles 52, 54 each have a cylindrical grip area configured to be held by hand, but the handles 52, 54 can each have other shapes.

Figure 17:
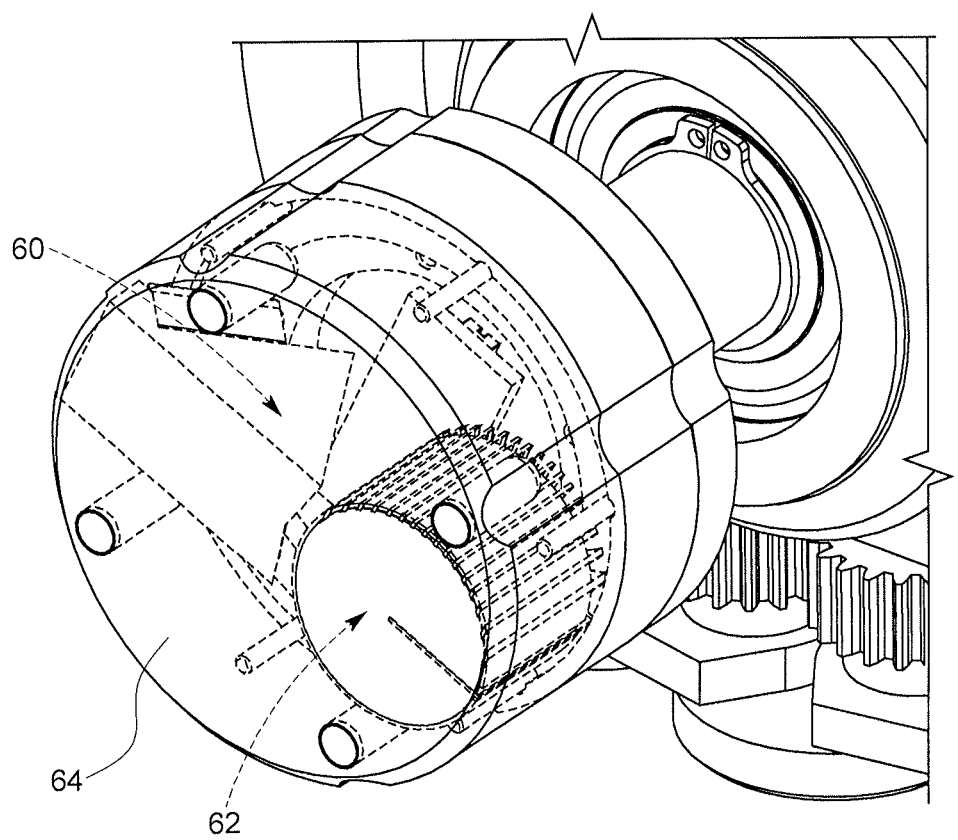
FIG. 17 is a perspective view of an end portion of the probe of FIG. 14.

The probe 50 also has an inspection portion 56 at a distal end thereof. The inspection portion 56 is configured to be inserted into a stud hole of a solid axle such that an end face 58 of the probe 50, which is substantially flat, abuts an end face of the stud hole, which can also be substantially flat. The probe 50 includes at least one ultrasonic transducer 60, 62 in the inspection portion 56, as also shown in FIG. 17. The at least one ultrasonic transducer 60, 62 is at the end face 58 to facilitate ultrasound wave generation in the solid axle to which the probe 50 is operatively coupled, e.g., the solid axle into which the inspection portion 56 is inserted. In this illustrated embodiment, the at least one ultrasonic transducer 60, 62 includes an angle beam UT PA transducer 60 configured to generate shear waves and a longitudinal beam UT PA transducer 62 configured to generate compression waves. The angles of the shear and compression waves can vary, as discussed above.

The probe 50 has a plexiglass (or similar) cover 64 at its distal end through which the angle beam UT PA and longitudinal UT PA transducers 60, 62 are configured to propagate their respective ultrasonic waves. In use, a couplant (e.g., a paste or a fluid such as water, grease, oil, a gel, etc.) can be provided on the end face 58 on the cover 64 to facilitate propagation of the UT signals. In the case of a low viscosity fluid couplant, one or more openings in the cover 64 can be present to allow the couplant flow to the front of the end face 58. In an embodiment, external pumps could recirculate the couplant through the system by delivering the couplant to the front of the end face 58. Following delivery, the couplant can be recovered then re-delivered to the front of the end face 58.

Figure 18:
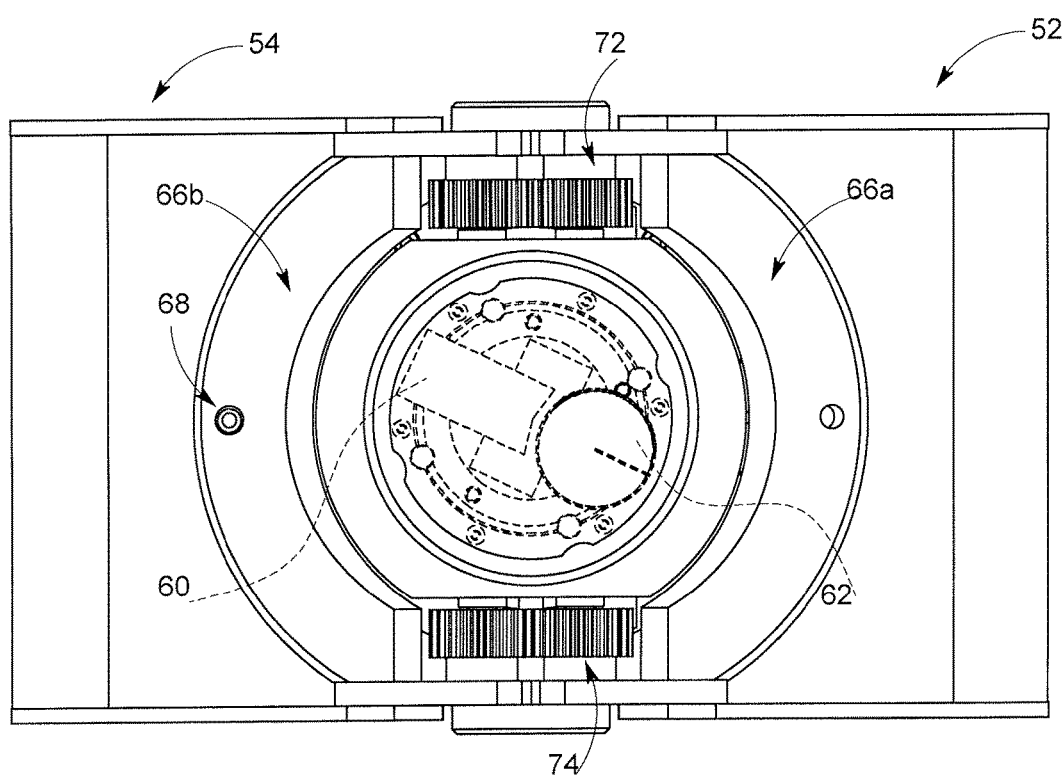
FIG. 18 is an end view of the probe of FIG. 14.

The probe 50 includes a coupling member configured to facilitate secure, releasable engagement of the probe 50 with a solid axle. In general, the coupling member is configured to hold the inspection portion 56 in alignment within the solid axle's stud hole, which may help ensure that the ultrasonic waves generated by the at least one ultrasonic transducer 60, 62 are properly propagated without unintentionally repeating angles of inspection and/or may allow the probe's position relative to the solid axle during use of the probe 50 not be entirely reliant on a user's potentially unstable manual positioning of the probe 50. In this illustrated embodiment, the coupling member includes a pair of magnets 66a, 66b, as shown in FIGS. 14 and 18, although the coupling member can include any number of magnets. The magnets 66a, 66b each have an arc shape to facilitate engagement thereof with a front face of a solid axle, which typically has a circular ring shape, as shown for example by the front face 18 of the axle 16 of FIGS. 3 and 4. The magnets 66a, 66b can, however, have other shapes.

The probe 50 includes at least one sensor 68 configured to sense a position of the probe 50 relative to a solid axle, such as one or more inductive sensors (also referred to as inductive proximity sensors) configured to sense proximity of the probe 50 to the metal solid axle. The at least one sensor 68 may help ensure that the probe 50 is properly operatively coupled to the solid axle by sensing engagement of the magnets 66a, 66b with the solid axle's front face. The at least one sensor 68 can thus be located on the coupling member (on one of the magnets 66b in this illustrated embodiment) on a surface thereof that contacts the front face.

As mentioned above, the first and second handles 52, 54 are configured to move. The movement of the handles 52, 54, which is illustrated in FIG. 18, is configured to cause movement of an engagement portion 70 of the probe 50 that includes the coupling member (the magnets 66a, 66b). The movement of the handles 52, 54 is thus configured to cause movement of the coupling member (the magnets 66a, 66b). The first and second movable handles 52, 54 are configured to move to facilitate operative coupling of probe 50 with the solid axle by helping to ensure that the coupling member (the magnets 66a, 66b) engage the solid axle's front face.

Figure 19:
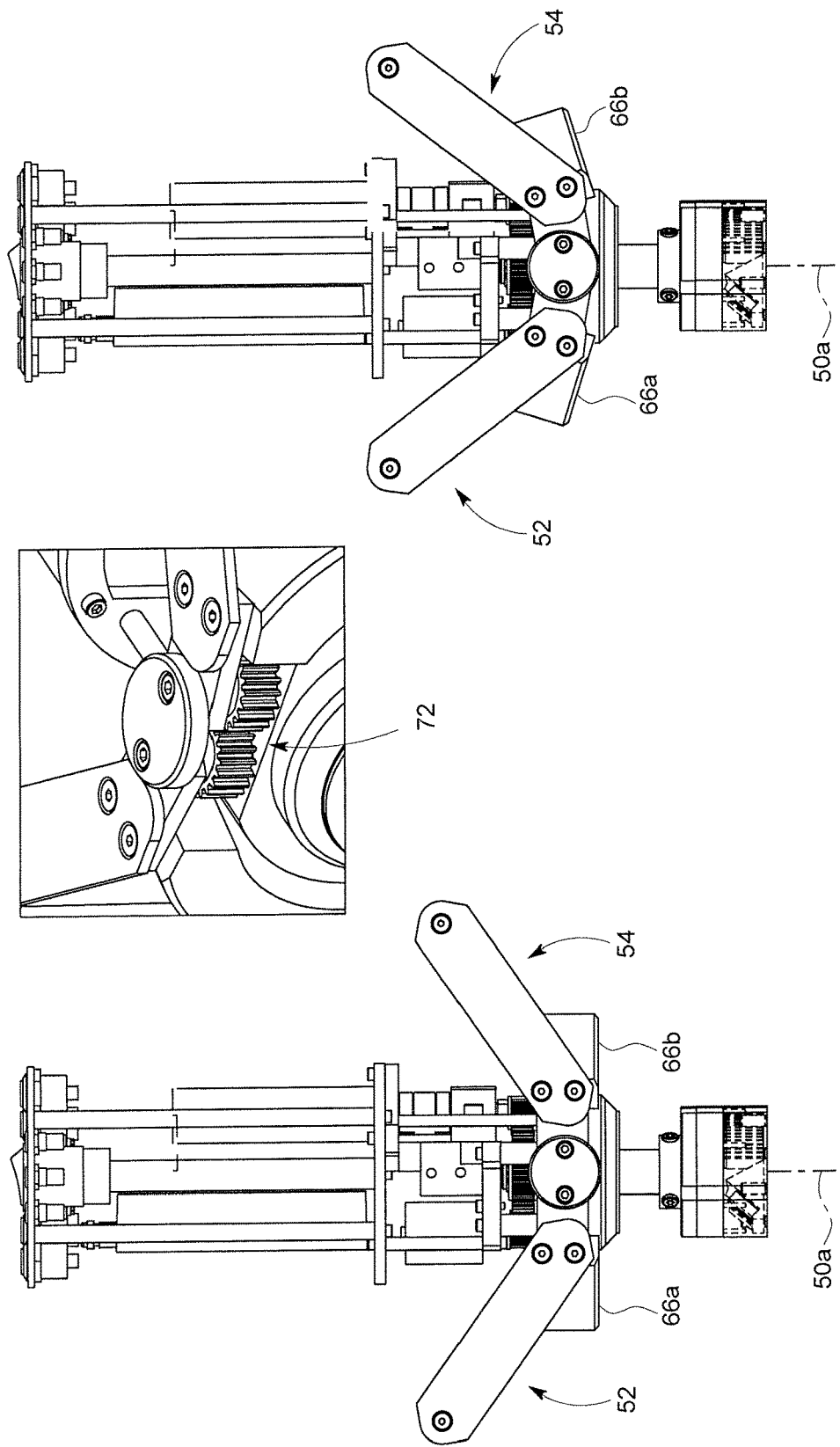
FIG. 19 is a top view of the probe of FIG. 14 with handles thereof in first and second positions.

In the illustrated embodiment, the handles 52, 54 are configured to move between a first, initial position, shown on a right hand side of FIG. 19, and a second, engagement position, shown in FIGS. 14-16 and on a left hand side of FIG. 19. In the first position, the handles 52, 54 are at a first angle relative to a longitudinal axis 50A of the probe 50, and the magnets 66a, 66b are angled relative to one another and are each angled away from the probe's end face 58. In the second position, the handles 52, 54 are at a second, larger angle relative to the longitudinal axis 50A of the probe 50, and the magnets 66a, 66b are not angled relative to one another, e.g., are at a zero angle relative to one another, and are not angled relative to the probe's end face 58, e.g., are at a zero angle relative to the end face 58. In this way, when the end face 58 abuts a corresponding surface of a solid axle (e.g., a bottom surface of the axle's stud hole) and the handles 52, 54 are in the first position, the magnets 66a, 66b will not engage the solid axle's front face. Similarly, when the end face 58 abuts the corresponding surface of the solid axle and the handles 52, 54 are in the second position, the magnets 66a, 66b will engage the solid axle's front face, e.g., magnetically engage the front face, and consequently help hold the probe 50 in position relative to the solid axle. Thus, in use, the inspection portion 56 of the probe 50 can be inserted into the solid axle's stud hole with the handles 52, 54 in the first position, and then the handles 52, 54 can be moved (e.g., by hand) from the first position to the second position to cause the magnets 66a, 66b to magnetically couple to the solid axle's front face. The inspection portion 56 of the probe 50 can thus be inserted into the stud hole at any rotational orientation relative thereto since the magnets 66a, 66b radially arranged around the location of the stud hole will be able to magnetically engage the axle's front face regardless of their rotational orientation relative thereto. Similarly, the handles 52, 54 can be moved from the second position to the first position to disengage the magnets 66a, 66b from the solid axle's front face.

To facilitate movement of the handles 52, 54 between the first and second positions, the probe 50 includes a pair of gear transmissions 72, 74, shown in FIGS. 18 and 19, although similar mechanisms may be used. The gear transmissions 72, 74 may help ensure that the handles 52, 54 move together, and hence that the magnets 66a, 66b move together.

Figure 20:
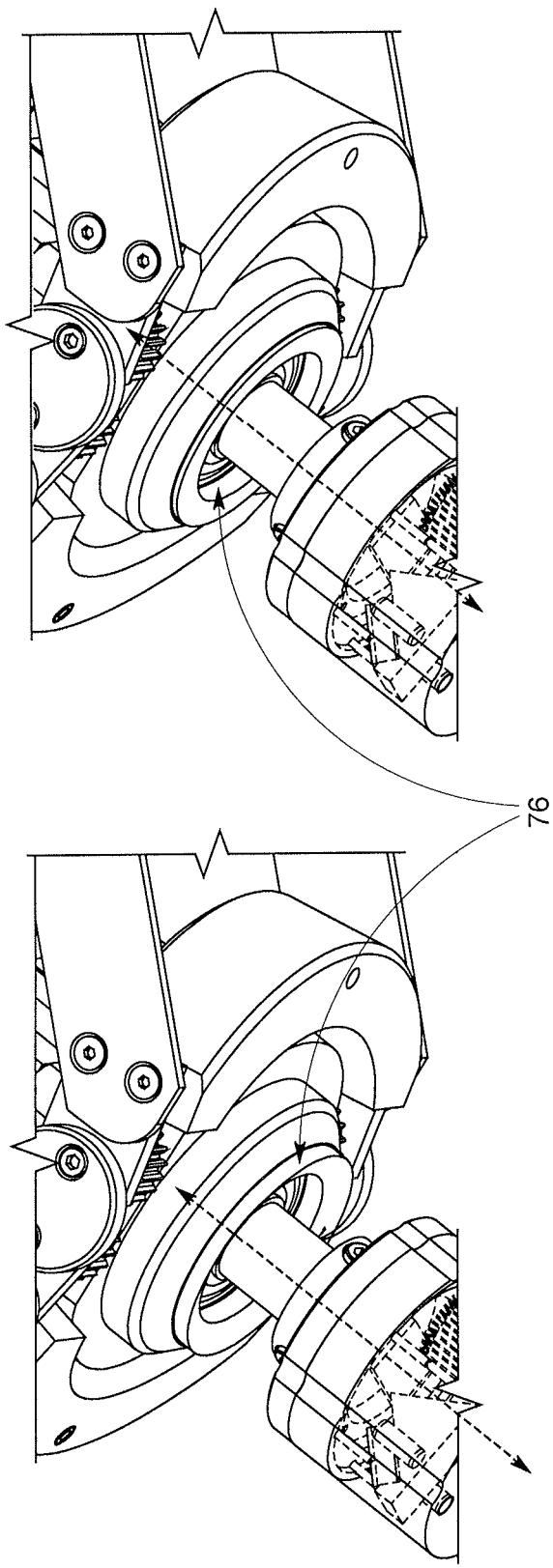
FIG. 20 is a perspective view of an intermediate portion of the probe of FIG. 14 with an engagement member thereof in first and second positions.

The probe 50 also includes an engagement member configured to engage the solid axle to which the probe 50 is operatively coupled to help press the inspection portion 56 of the probe 50 within the axle's stud hole, e.g., help press the end face 58 against the stud hole's bottom surface. The inspection portion 56 being pressed into the stud hole may help ensure a stable UT coupling. In the illustrated embodiment, as shown in FIGS. 14 and 20, the engagement member includes a spring loaded member 76 in the form of a ring located radially inward of the coupling member, e.g., radially inward of the magnets 66a, 66b. The spring loaded member 76 is configured to move between a first, distal position, shown on a left hand side of FIG. 20, and a second, proximal position, shown in FIG. 14 and on a right hand side of FIG. 20. The first, distal position is the default position of the spring loaded member 76, e.g., the position to which the spring loaded member 76 is biased by spring force. The spring loaded member 76 is thus biased in a distal direction toward the inspection portion 56. The spring loaded member 76 is configured to automatically move from the first position to the second position in response to the inspection portion 56 being inserted into a stud hole of a solid axle by virtue of the inspection portion 56 being pressed against the stud hole's bottom surface. Similarly, the spring loaded member 76 is configured to automatically move from the second position to the first position in response to the inspection portion 56 being removed from the stud hole by virtue of the inspection portion 56 being released from engagement with the stud hole's bottom surface.

Figure 21:
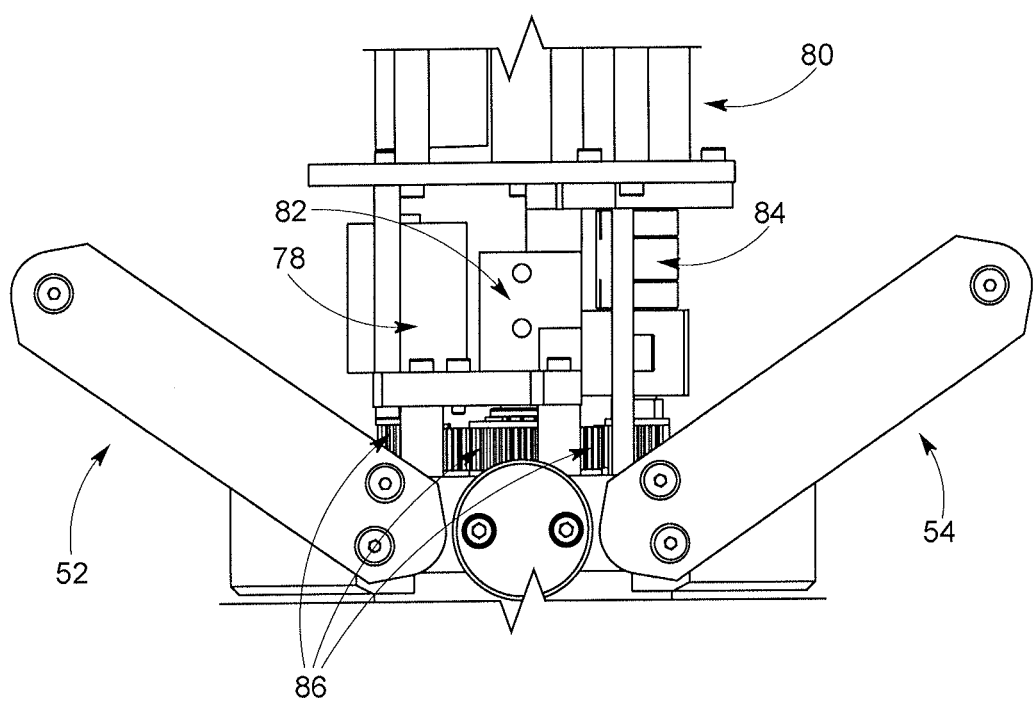
FIG. 21 is a top view of another intermediate portion of the probe of FIG. 14.
Figure 22:
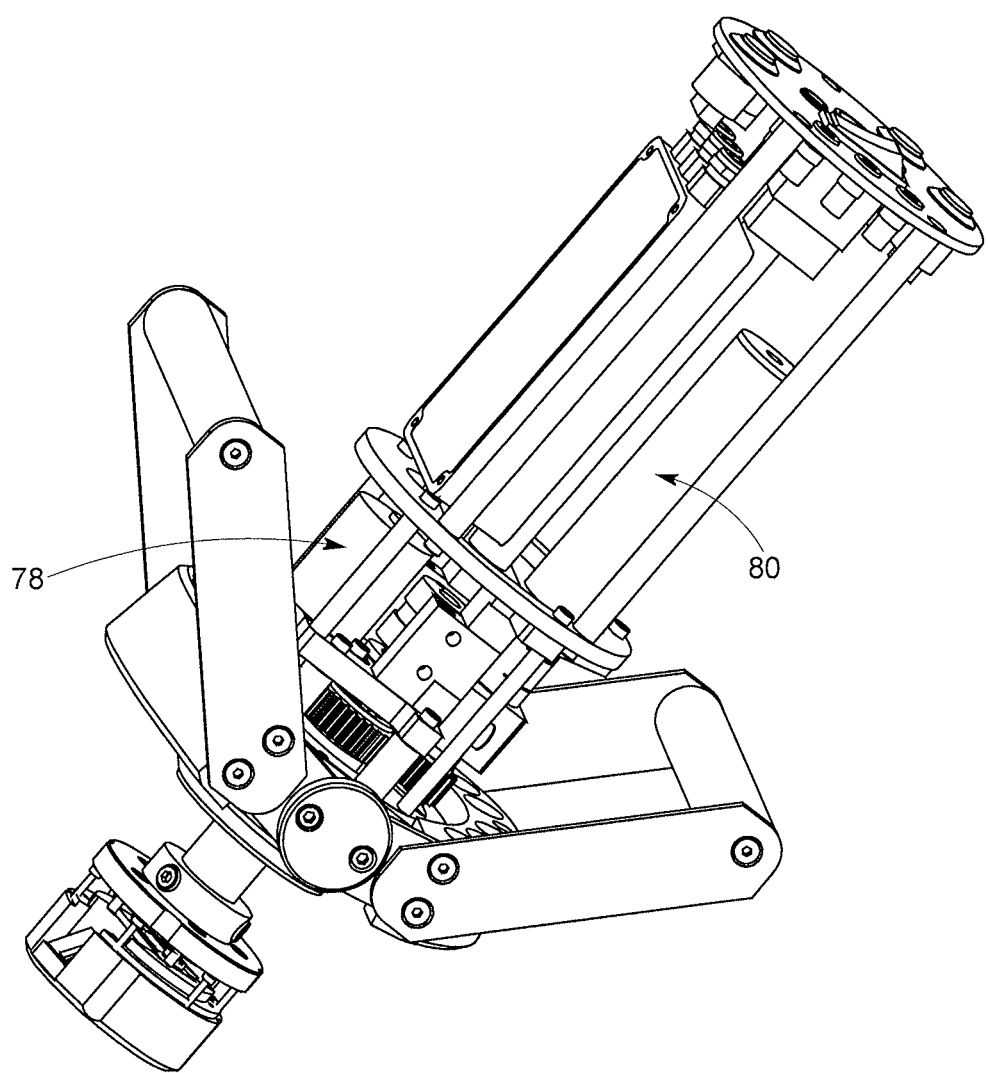
FIG. 22 is another perspective view of the probe of FIG. 14.

As shown in FIGS. 21 and 22, the probe 50 includes an encoder 78, a motor 80 (which is a DC motor in this illustrated embodiment), at least one position sensor 82, an elastic joint 84, and a gear transmission 86 from the motor 80 to a main shaft and an encoder shaft on which the encoder 78 is mounted. The at least one position sensor 82, which includes two position sensors in this illustrated embodiment, is configured to sense a position of the probe 50 relative to the solid axle to which the probe 50 is operatively coupled. The encoder 78 is configured to convert the signals of the at least one position sensor 82 to an electronic signal for transmission to a controller 88 of the probe 50, as shown in FIG. 23, to help determine positioning of the probe 50 relative to the solid axle.

Figure 23:
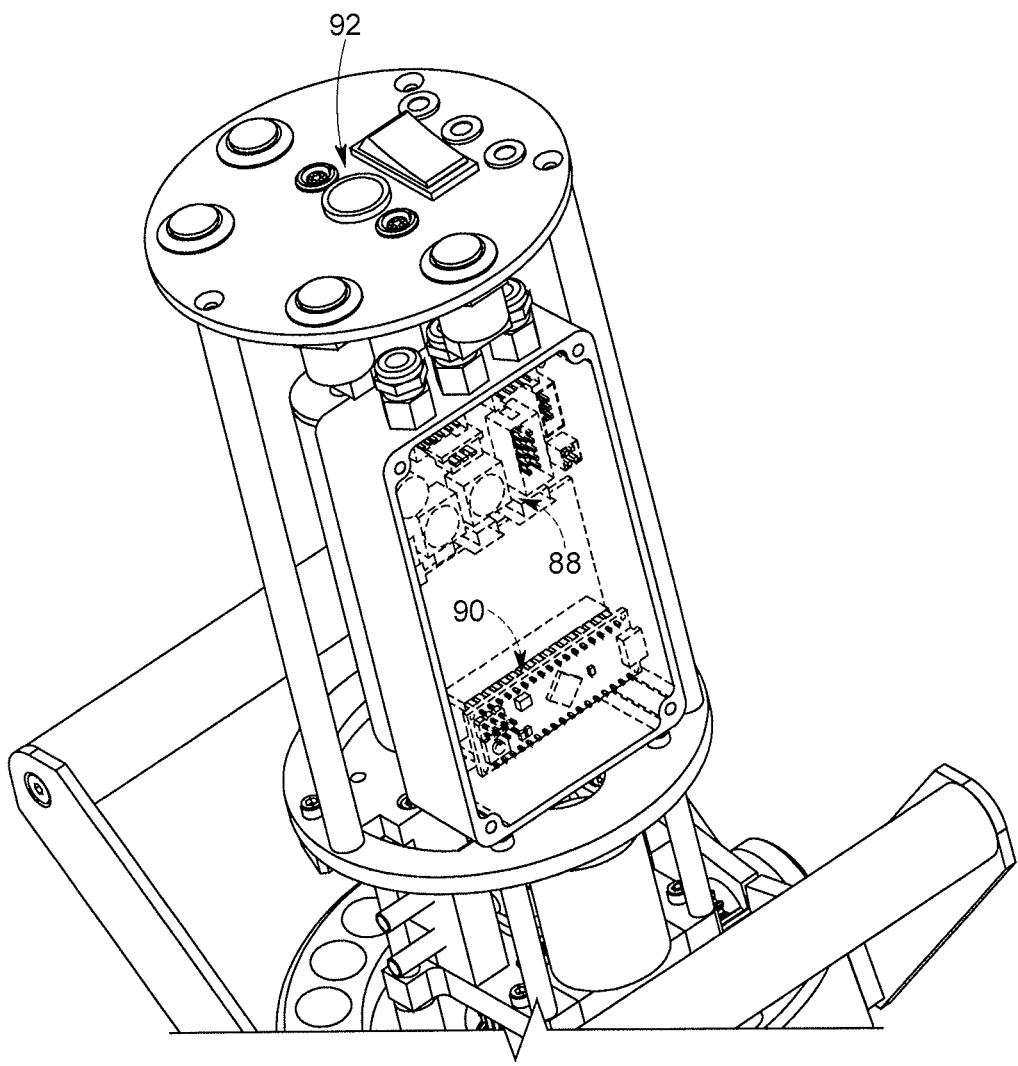
FIG. 23 is a perspective view of a front portion of the probe of FIG. 14.

As also shown in FIG. 23, the probe 50 includes a memory 90 configured to store positions of the probe 50 previously sensed by the encoder of the DC motor 80. The controller 88 is configured to use the electronic signal received from the position sensor 84 and the encoder of the DC motor 80 to determine, based on the previously sensed positions of the probe 50, whether the probe 50 has rotated a full 360° relative to the solid axle to ensure complete gathering of UT data. If the controller 88 determines the probe 50 has not yet rotated 360°, then the controller 88 is configured to actuate the motor 80 (to turn on the motor 80 or to not yet turn off the motor 80) to cause movement of the gear transmission 86, e.g., to cause gears of the gear transmission 86 to rotate, thereby causing rotation of the inspection portion 56 within the solid axle's stud hole. If the controller 88 determines the probe 50 has rotated 360°, then the controller 88 causes motor 80 to stop, thereby stopping rotation of the inspection portion 56 within the solid axle's stud hole. The controller 88 can be configured to stop the motor 80 upon achievement of 360° rotation of the inspection portion 56, which may help save time by rotating only as much as needed, or at some amount of rotation over 360°, which may help ensure that complete data is acquired.

Instead of being rotated via the motor 80, the probe 50 can be manually rotated. Electronic rotation may, however, result in more stable and consistent rotation of the probe 50 within the solid axle's stud hole and thereby help ensure that complete UT data is acquired along the axle's entire skin surface.

Figure 24:
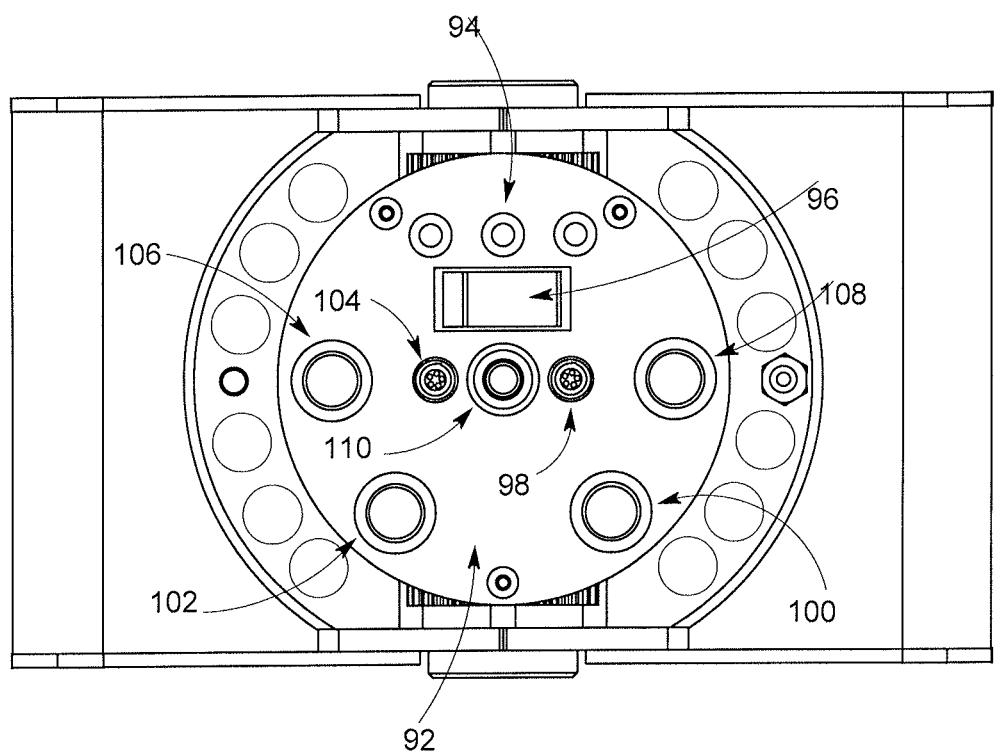
FIG. 24 is a front end view of the probe of FIG. 14.
Figure 25:
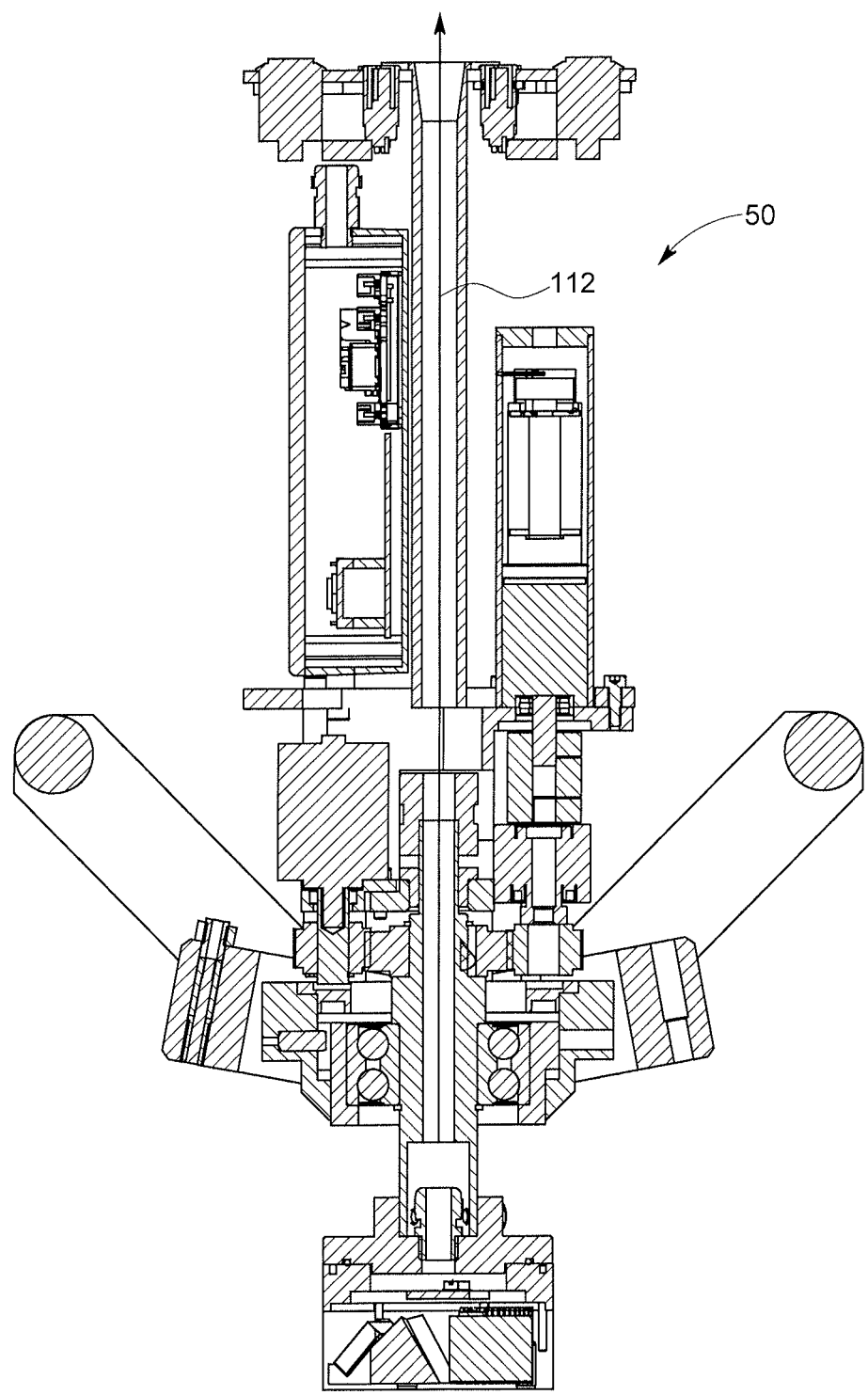
FIG. 25 is a cross-sectional view of the probe of FIG. 14.

As shown in FIGS. 23 and 24, the probe 50 includes a user interface portion 92. In general, the user interface portion 92 is configured to facilitate user control and monitoring of the probe 50. The user interface portion 92 can have a variety of configurations but in this illustrated embodiment includes at least one status indicator 94, a speed selector 96 configured to allow user selection of a speed of the motor 80 (and hence a speed of the inspection portion's rotation), an encoder socket 98 configured to operatively couple to a cable for the encoder 78, a stop/reset button 100 to allow a user to stop any inspection underway and cause position of the probe 50 to be re-sensed by the at least one position sensor 82 and adjusted if necessary via the motor 80, an inspect button 102 configured to begin a 360° rotation 104 of the probe 50 in the stud hole, a power supply socket 104 configured to operatively couple to a power supply cable, a left movement button 106 configured to allow a user to cause movement of the probe 50 to the left to manually adjust position of the probe 50 within a stud hole, and a right movement button 108 configured to allow a user to cause movement of the probe 50 to the right to manually adjust position of the probe 50 within a stud hole. The at least one status indicator 94 in this illustrated embodiment includes a plurality of LED lights. One of the LED lights (Insp.) is configured to be illuminated when the probe 50 is ready for inspection, e.g., signals from the at least one ultrasonic transducer 62, 64 can be recorded in the accompanied UT electronics, one of the LED lights (PWR) is configured to be illuminated when the probe 50 is powered on, and one of the LED lights (Fault) is configured to illuminate in the event of an error detected by the controller 88 (e.g., the probe 50 not being coupled to the solid axle's front face as determined by an inductive sensor 68, etc.). Also, a UT cable exit 110 is present through which a UT cable operatively coupled to the at least one ultrasonic transducer 62, 64 exits the probe 50 by which the at least one ultrasonic transducer 62, 64 can be connected to UT electronics recording and displaying the UT signals of the inspection and thus forming a complete inspection system. As shown in FIG. 25, the probe 50 includes a main shaft 112 configured to have the UT cable disposed therein. The main shaft 112 can include other elements therein, such as a tube extending therethrough into which the couplant can be introduced for release onto the end face 58. In another embodiment, the UT cables can also be connected to a slip-ring system to let the probe head rotate endlessly. In such a case, the slip-ring can be mounted on the central shaft, and the external housing of the slip ring can be fixed on the flange where the motor is mounted.

Figure 26:
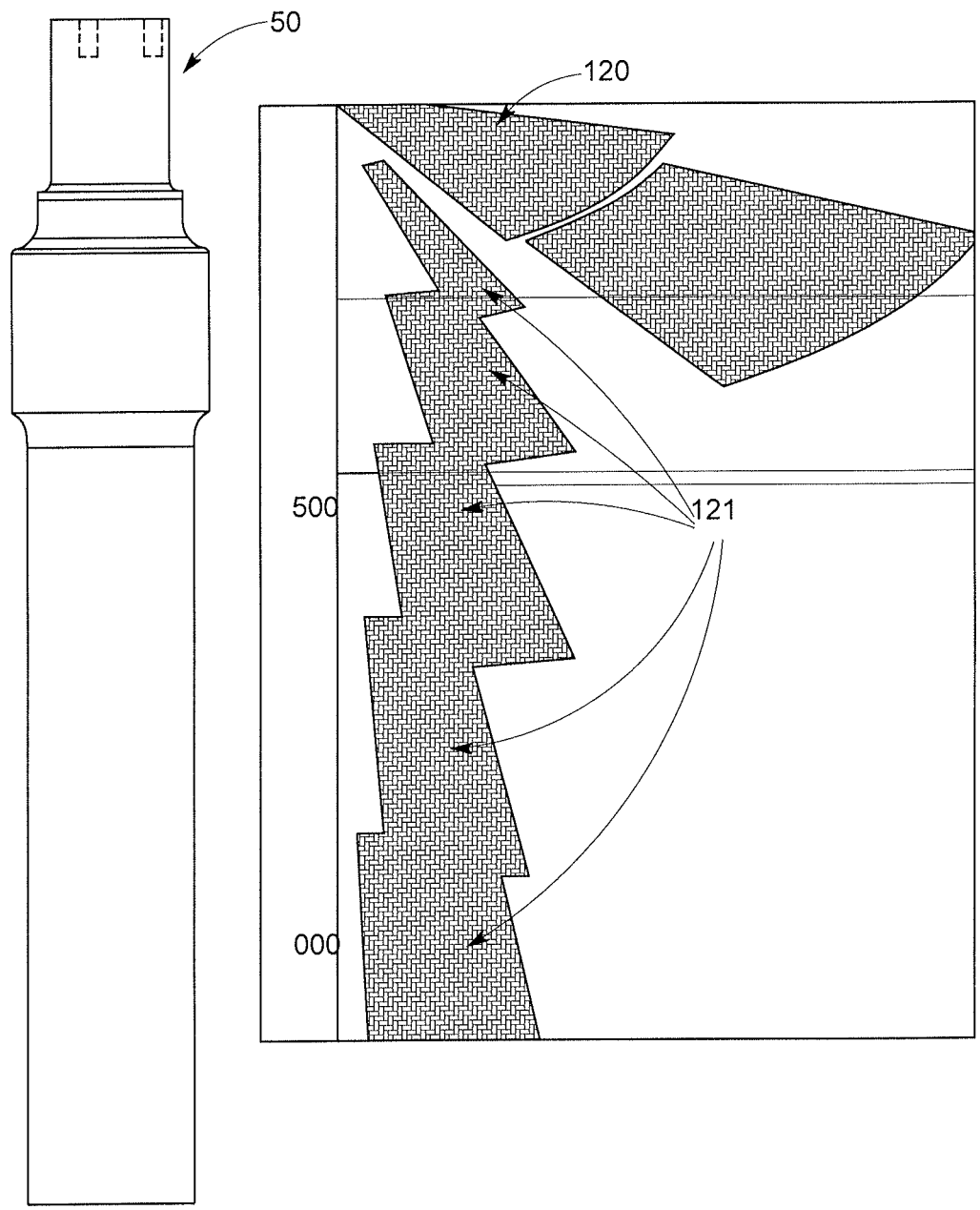
FIG. 26 is an image of ultrasonic wave groups for the solid axle of FIG. 13.

FIG. 26 illustrates one configuration of an actuation and evaluation unit configured to control a transducer and configured to receive, process, and display the signals received from transducers in a multi-group setup (e.g., a group including the ultrasonic transducers 62, 64). In the illustrated setup and display, a probe is operated in a multi-group setup in which the S-Scan 120, 121 of each group covers a specific surface area of the solid axle 50 (though other embodiments of solid axles can be similarly scanned), as indicated in FIG. 26. By employing a multi-group setup, the groups can be configured such that misleading geometrical reflections or reflections originating in mode conversions can be discriminated based on inspection range and steering range such that they do not mimic false indications.

Figure 27:
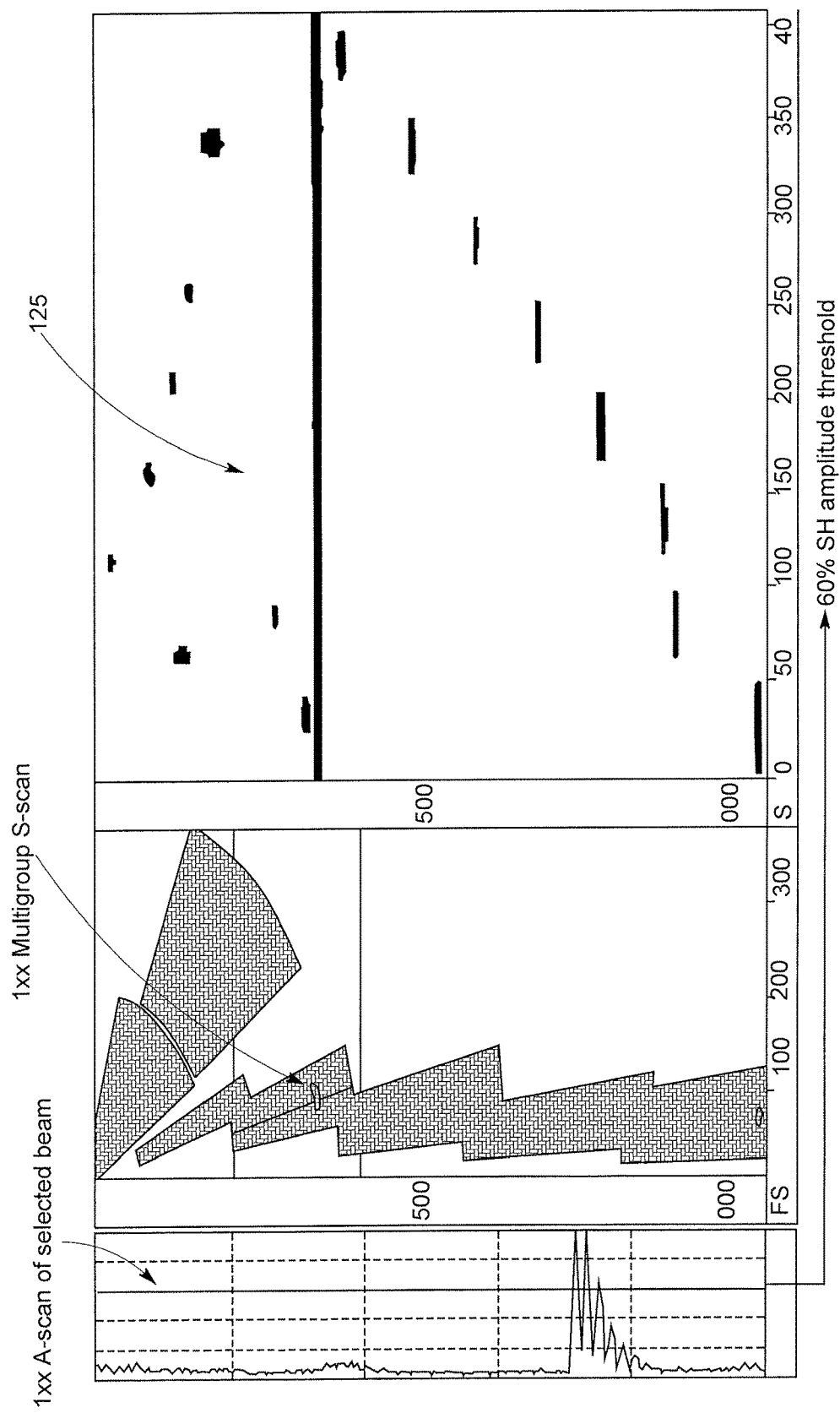
FIG. 27 is an image of A-Scan, Multigroup S-Scan, and Position Encoded B-Scan data.
Figure 28:
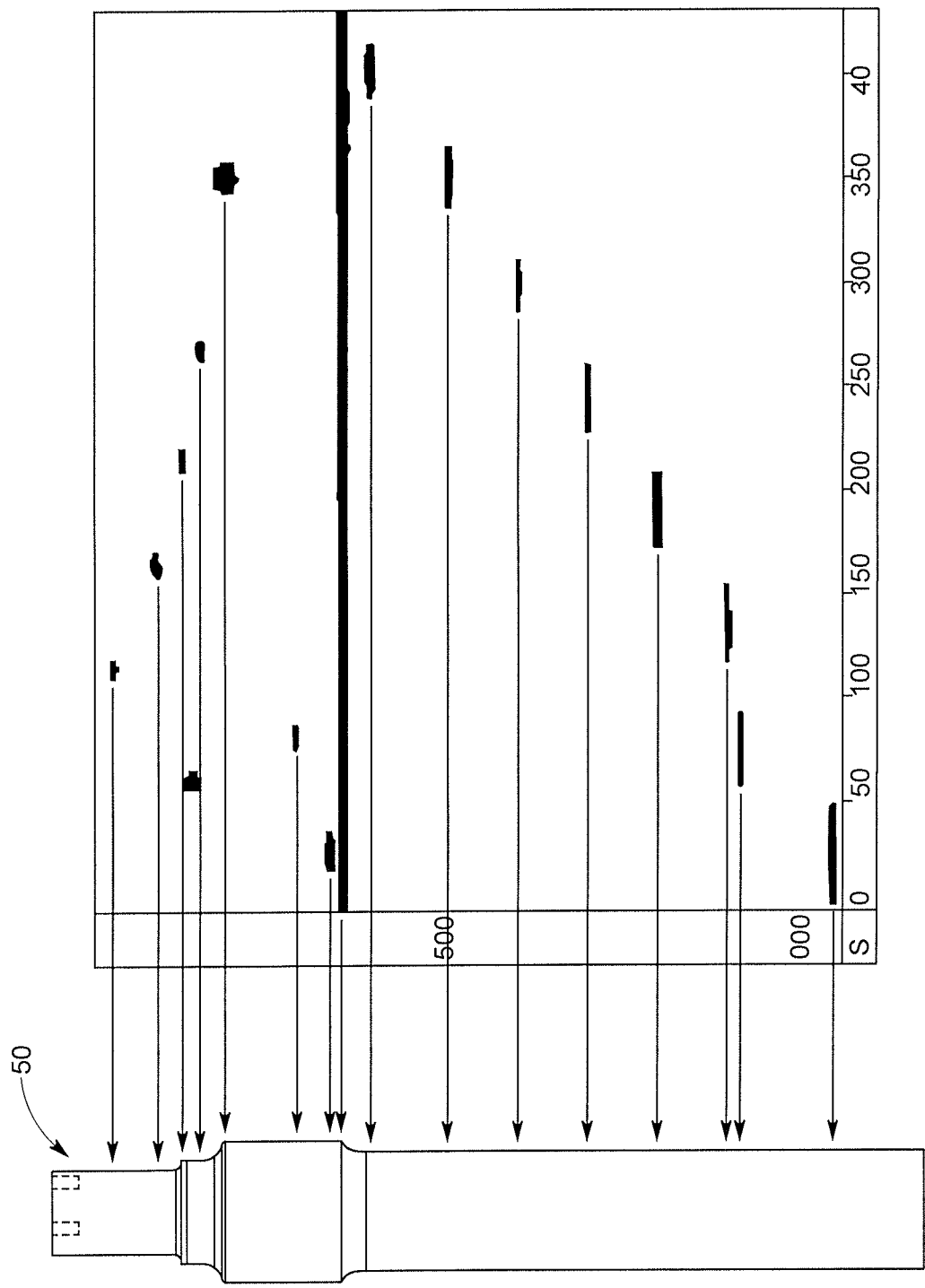
FIG. 28 is an image of single indications of the B-Scan data of FIG. 27 mapped to the skin surface of the solid axle of FIG. 13.

FIG. 27 illustrates an example of position encoded B-Scan data 125 from the solid axle 50 (though other embodiments of solid axles can be similarly scanned) recorded with the actuation and evaluation unit of FIG. 26 to display the inspection results. The B-Scan displays the covered skin surface of the solid axle 50 and shows detected indications based on depth along the longitudinal direction of the axis and angular position. FIG. 28 illustrates an example of how the single indications on the B-Scan can be mapped to the actual skin surface of the solid axle 50.

The devices, systems, and methods disclosed herein produce a number of advantages and/or technical effects in addition to or in alternative to any one or more of those discussed above. As an example, a probe operatively coupled to a solid axle may allow for inspection of substantially an entire skin surface of the axle. The probe being configured to generate ultrasonic shear waves and longitudinal compression waves may facilitate this inspection. As another example, a probe being configured to access a solid axle via a front face thereof allows for the inspection even if the solid axle's skin surface is protected with a coating such as paint. As yet another example, a probe being configured to gather and store data such as positional data may facilitate later analysis of use of the probe and/or may facilitate real time positioning of the probe using the stored data. As still another example, a probe using UT PA transducer(s) and being connected to an actuation and evaluation unit configured to receive, process, and display the signals received from the ultrasonic transducers may allow advanced data acquisition techniques such as S-Scan, A-Scan, B-Scan, and C-Scan representations of the UT inspection data. In the B-Scan analysis, only reflections from real indications may be present (e.g., geometrical reflections may be avoided) by using multiple groups distinct in steering range, depth, and reference gain to achieve a zone-discrimination along a length of the axle.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An inspection system, comprising:
   a probe configured to be inserted into a blind hole extending through a front face of a solid axle, the probe including an ultrasonic transducer at an end face thereof that is configured to generate ultrasonic waves in the solid axle covering substantially an entire portion of the solid axle to be inspected when the probe is within the blind hole;
   a securing element including at least one magnet positioned radially outward of the ultrasonic transducer, the securing element configured to releasably engage the front face of the solid axle; and
   an engagement member including an annular, spring loaded member positioned radially inward from the securing element and configured to position the ultrasonic transducer within the blind hole.

2. The inspection system of claim 1, wherein the ultrasonic transducer includes an angle beam ultrasonic transducer configured to propagate a shear wave and a longitudinal beam ultrasonic transducer configured to propagate a compression wave, and the ultrasonic waves include the shear wave propagated by the angle beam ultrasonic transducer and the compression wave propagated by the longitudinal beam ultrasonic transducer.

3. The inspection system of claim 1, wherein the probe is configured to be inserted into the blind hole until the end face of the probe abuts a bottom surface of the blind hole.

4. The inspection system of claim 1, wherein the probe includes a controller configured to analyze the echo to determine whether a flaw is present in the solid axle.

5. The inspection system of claim 4, wherein the flaw includes at least one of a crack, a notch, an inclusion, a void, or a fracture.

6. The inspection system of claim 1, wherein the substantially entire portion of the solid axle to be inspected is at least one of substantially an entire skin surface of the solid axle or substantially an entire volume of the solid axle.

7. The inspection system of claim 1, further comprising a liquid couplant on the end face of the probe.

8. The inspection system of claim 7, wherein the liquid couplant includes one of water, grease, oil, or a gel.

9. The inspection system of claim 1, wherein the ultrasonic transducer includes a plurality of phased array transducers configured to operate with different wave modes and configured to provide a zone-discrimination employed an actuation and evaluation unit during position encoded recording of a B-Scan of the axle's skin surface.

10. The inspection system of claim 1, wherein the ultrasonic transducer includes a single ultrasonic transducer.

11. The inspection system of claim 1, wherein the probe is configured to be inserted into the blind hole at any rotational orientation relative to the solid axle.

12. The inspection system of claim 1, wherein the probe is configured to be automatically centered within the blind hole when inserted therein.

13. The inspection system of claim 1, wherein the spring loaded member is biased in a first distal direction and configured to automatically move from the first distal position to a second proximal position responsive to inserting the probe into the blind hole.

14. An inspection method, comprising:
  inserting a probe, including an ultrasonic transducer, into a blind hole extending through a front face of a solid axle;
  engaging the ultrasonic transducer with the solid axle via an engagement member including an annular, spring loaded member configured to position the ultrasonic transducer within the blind hole;
  securing the probe within the blind hole by a securing element including at least one magnet positioned radially outward of the ultrasonic transducer, the securing element configured to releasably engage the front face of the solid axle and positioned radially outward of the annular spring loaded member; and
  activating the ultrasonic transducer of the probe to cause ultrasonic waves to propagate within the solid axle covering at least one of substantially an entire skin surface of the solid axle or substantially an entire volume of the solid axle.

15. The method of claim 14, wherein the ultrasonic transducer includes an angle beam ultrasonic transducer and a longitudinal beam transducer, and the ultrasonic waves include a shear wave propagated by the angle beam ultrasonic transducer and a compression wave propagated by the longitudinal beam ultrasonic transducer.

16. The method of claim 14, wherein the probe is inserted into the blind hole until an end face of the probe abuts a bottom surface of the blind hole.

17. The method of claim 14, wherein the probe is automatically centered within the blind hole when inserted therein.

18. The method of claim 14, further comprising detecting an echo of the ultrasonic waves, and analyzing the echo to determine whether a flaw is present in the solid axle.

19. The method of claim 18, wherein the flaw includes at least one of a crack, a notch, an inclusion, a void, or a fracture.

20. The method of claim 14, further comprising removing the probe from the blind hole;
  inserting the probe into a second blind hole formed in a second solid axle; and
  activating the ultrasonic transducer of the probe to cause ultrasonic waves to propagate within the second solid axle covering at least one of substantially an entire skin surface of the solid axle or substantially an entire volume of the solid axle.

21. The method of claim 14, wherein, responsive to engaging the probe with the solid axle, the annular, spring loaded member automatically moves from a first distal position for which the annular, spring loaded member is biased, to a second proximal position.

* * * * *